United States Patent [19]
Layman et al.

[11] Patent Number: 5,712,795
[45] Date of Patent: Jan. 27, 1998

[54] POWER MANAGEMENT SYSTEM

[75] Inventors: Douglas C. Layman; Oliver J. Smith, both of San Diego, Calif.

[73] Assignee: Alaris Medical Systems, Inc., San Diego, Calif.

[21] Appl. No.: 538,096

[22] Filed: Oct. 2, 1995

[51] Int. Cl.$^6$ ........................................... H02J 7/04
[52] U.S. Cl. .................. 364/472; 320/35; 320/39; 320/48; 320/20; 307/64; 307/65; 307/66; 307/85; 340/636; 324/426; 324/431
[58] Field of Search .................. 364/492; 320/35, 320/39, 48, 20; 307/64, 65, 66, 85, 86, 96, 97; 340/636; 324/426, 431

[56] References Cited

U.S. PATENT DOCUMENTS

| | | | |
|---|---|---|---|
| 3,925,772 | 12/1975 | Miller et al. | 340/253 |
| 4,468,571 | 8/1984 | Heavey et al. | 307/66 |
| 4,673,826 | 6/1987 | Masson | 307/66 |
| 4,779,050 | 10/1988 | Ohnari | 324/426 |
| 4,782,241 | 11/1988 | Baker et al. | 307/66 |
| 4,820,966 | 4/1989 | Fridman | 320/32 |
| 4,876,513 | 10/1989 | Brilmyer et al. | 324/426 |
| 4,952,862 | 8/1990 | Biagetti et al. | 320/48 |
| 5,019,717 | 5/1991 | McCurry et al. | 307/66 |
| 5,057,697 | 10/1991 | Hammond et al. | 307/66 |
| 5,117,324 | 5/1992 | Jonhson, Jr. | 307/66 |
| 5,148,043 | 9/1992 | Hirata et al. | 307/66 |
| 5,182,518 | 1/1993 | Stich et al. | 324/511 |
| 5,295,078 | 3/1994 | Stich et al. | 364/483 |
| 5,321,392 | 6/1994 | Skakoon et al. | 340/636 |
| 5,347,164 | 9/1994 | Yeh | 307/66 |
| 5,381,350 | 1/1995 | Fiorina et al. | 364/550 |
| 5,475,294 | 12/1995 | Isoda | 320/14 |
| 5,545,969 | 8/1996 | Hasegawa | 320/35 |

FOREIGN PATENT DOCUMENTS

| | | | |
|---|---|---|---|
| 0 458 232 A2 | 11/1991 | European Pat. Off. | H02J 7/00 |
| 648 936 A5 | 4/1985 | Switzerland | G01R 31/36 |

Primary Examiner—James P. Trammell
Assistant Examiner—Hien Vo
Attorney, Agent, or Firm—Fulwider Patton Lee & Utecht, LLP

[57] ABSTRACT

A power management system automatically manages the power to operate a biomedical device, such as an infusion pump containing an internal battery. When external power is available, the management system operates the biomedical device from the external power and controls a recharger to maintain the battery at full charge. The power management system automatically calculates battery charge status and use and provides a run time display of the calculated amount of time that the battery can operate the biomedical device under current power requirements of the biomedical device. The power management system automatically updates the calculated charge status of the battery as well as the calculated capacity of the battery based on environmental factors and battery characteristics. The power management system automatically and periodically performs a deep discharge/recharge cycle to refresh the battery.

52 Claims, 24 Drawing Sheets

POWER MANAGEMENT SYSTEM

BACKGROUND OF THE INVENTION

The invention relates generally to managing a power supply system, and more particularly relates to management of a power supply system having a battery for control over the charging of the battery and the determination of battery status.

Rechargeable batteries have provided an advancement in the art in that systems using such batteries have a greatly reduced need for battery replacement. Such systems may operate for many years on the same battery or batteries. Aside from the environmental benefit of the use of such batteries, their expense is typically lower because they can be reused after discharge and therefore have extended lives.

In some applications, the ability to operate on battery power is highly desirable. For example, where an infusion pump is used to supply fluid to a patient, it is desirable that the pump have an internal battery in case the patient must be moved to a different location during the infusion process. Interruption of an infusion to a patient is not desirable in many cases and the ability of the pump to continue operation during patient movement is desirable. In addition, an internal battery can keep the infusion process going should wall power be lost. Thus, many infusion pumps include a battery or batteries to support ambulatory or other operation. Unplugging the pump from wall power as the patient must be moved or a disruption in AC power causes the pump to immediately transition to its internal battery power to support its continued operation.

Rechargeable batteries are desirable for another reason. Busy hospital personnel typically prefer lower maintenance equipment. Changing batteries in infusion pumps not only would take their time, which they may prefer to spend elsewhere, but also means that the infusion pump is out of service until the battery change has been completed. Rechargeable batteries, and an automated system to cause the recharge process to be performed, are highly desirable as the maintenance requirements of the infusion pump effectively decrease.

However, batteries have a finite capacity and after completely discharging, the battery cannot support further operation of the infusion pump. While it is beneficial to be able to determine how much charge remains in a battery, it is more beneficial to determine the amount of time or "run-time" remaining in the battery. This then would indicate to the infusion pump operator the amount of time that the pump can be operated at the presently selected infusion rate with the existing battery. In the case where the indicated run time is greater than the predicted ambulatory time for the patient, the operator can then feel confident in engaging in ambulatory infusion of the patient with that pump. Such a run-time indicator feature is particularly helpful for certain rechargeable batteries, such as nickel-cadmium ("NiCd") type batteries, which experience an abrupt and severe voltage drop as the stored charge is depleted (as opposed to a more gradual voltage decrease with lead-acid batteries). Such an abrupt voltage drop will result in immediate pump cutoff with no warning. The run-time indicator will provide that warning so that the operator knows when to expect the abrupt end of battery power.

Determining battery run-time typically depends on multiple factors, at least for NiCd batteries. The amount of charge a battery can store, and therefore its run time, depends on the age of the battery, its charge/discharge history, as well as the temperature during charging. An additional factor includes consideration of the decrease in the battery capacity that can occur if the battery is allowed to only partially discharge before being recharged. Additionally, the run time of a battery directly depends on the current level being supplied by the battery. To provide an accurate run-time indicator, these factors and others should be considered.

Automatically controlled deep discharge cycles may refresh a NiCd battery and greatly prolong its service life thereby reducing the requirement for battery replacement. However, requiring operators to manually determine when such deep discharge cycles are necessary and to learn how to perform them is too great a requirement for hospital personnel. Additionally, during charging, some cells of a battery may be weaker than others, and lower level charging after a fast charging procedure may be necessary to bring the weaker cells up to full charge. Requiring hospital personnel to manually switch charge modes and monitor the charging process of a battery would be an excessive demand on their valuable time.

Because of the preference for low maintenance equipment, as mentioned above, a desirable feature for an infusion pump would be an automated power management system where replacement of the battery is required only after extended periods of use, such as years of use, and otherwise, the infusion pump itself controls the battery for battery recharging and refreshing, and monitors the battery for determination of the run time left in the battery.

Thus those skilled in the art have recognized a need for an automatic power management system that not only controls the recharging of a battery, but one that also automatically refreshes a battery to prolong its service life, monitors the charge status of the battery, and provides an accurate indication of the run-time of a battery. The present invention fulfills these needs and others.

SUMMARY OF THE INVENTION

Briefly and in general terms, the present invention is directed to a power management system that automatically manages the power supplied to a biomedical device. The system includes a rechargeable battery and automatically determines the power source used to supply power to the biomedical device. The system also automatically controls battery charging and provides a display of time remaining for biomedical device battery operation based on the current power requirements of the biomedical device.

In one aspect, the power management system automatically charges the battery to full charge whenever an external power source is connected to the system. In a more detailed aspect, four charging modes are available for use in charging the battery to full capacity. In a fast charge mode, the battery is charged at a constant, relatively high current rate. In a top-up charge mode, the battery is charged at a lower rate so that all cells reach full status. In a floating charge mode, energy lost due to self-discharge is replaced. When the ambient temperature exceeds a predetermined threshold, a hot charge mode is used to fully charge the battery.

In further detailed aspects, a processor monitors the capacity of the battery and calculates the charge remaining in the battery based on charging activities and usage. The processor also accounts for loss of battery charge through self-discharge and other effects. Based on the calculated amount of charge in the battery and the current power requirements of the biomedical device, the processor calculates the run time of the battery and displays the run time.

In another aspect, the processor lowers the capacity of the battery in accordance with the age of the battery, the ambient temperature at which the battery has been charged and the number of complete cycles of discharge/charge of the battery. The calculated battery capacity is used by the processor in calculating the amount of charge stored in the battery.

The power management system further comprises a temperature sensor for producing a temperature signal representative of the temperature of the battery and controls the charger in response to the temperature sensor so that the battery temperature remains within predetermined limits.

In another aspect, the processor in the power management system also automatically causes the battery to undergo a deep discharge cycle on a periodic basis to recondition the battery. The battery is discharged to a predetermined low voltage and is then recharged to full status. In a more detailed aspect, the battery powers the biomedical device when the device is operating at the time the battery if caused to undergo a deep discharge cycle.

In yet further aspects, the processor automatically determines a decrease in the value for the amount of charge in the battery based on a failure to complete a complete charging cycle and automatically determines an increase in the value for the amount of charge in the battery based on the completion of a complete charging cycle.

A display includes the run time gauge indicating in time increments how much time remains in the battery based on the current power usage of the biomedical device. A full icon indicating that the battery is fully charged is also included as is a battery empty icon to signify battery discharged status or deep discharge/recharge activities.

Other aspects and advantages of the invention will become apparent from the following detailed description and the accompanying drawings, illustrating by way of example, the features of the invention.

DETAILED DESCRIPTION OF PREFERRED EMBODIMENTS

Figure 1:
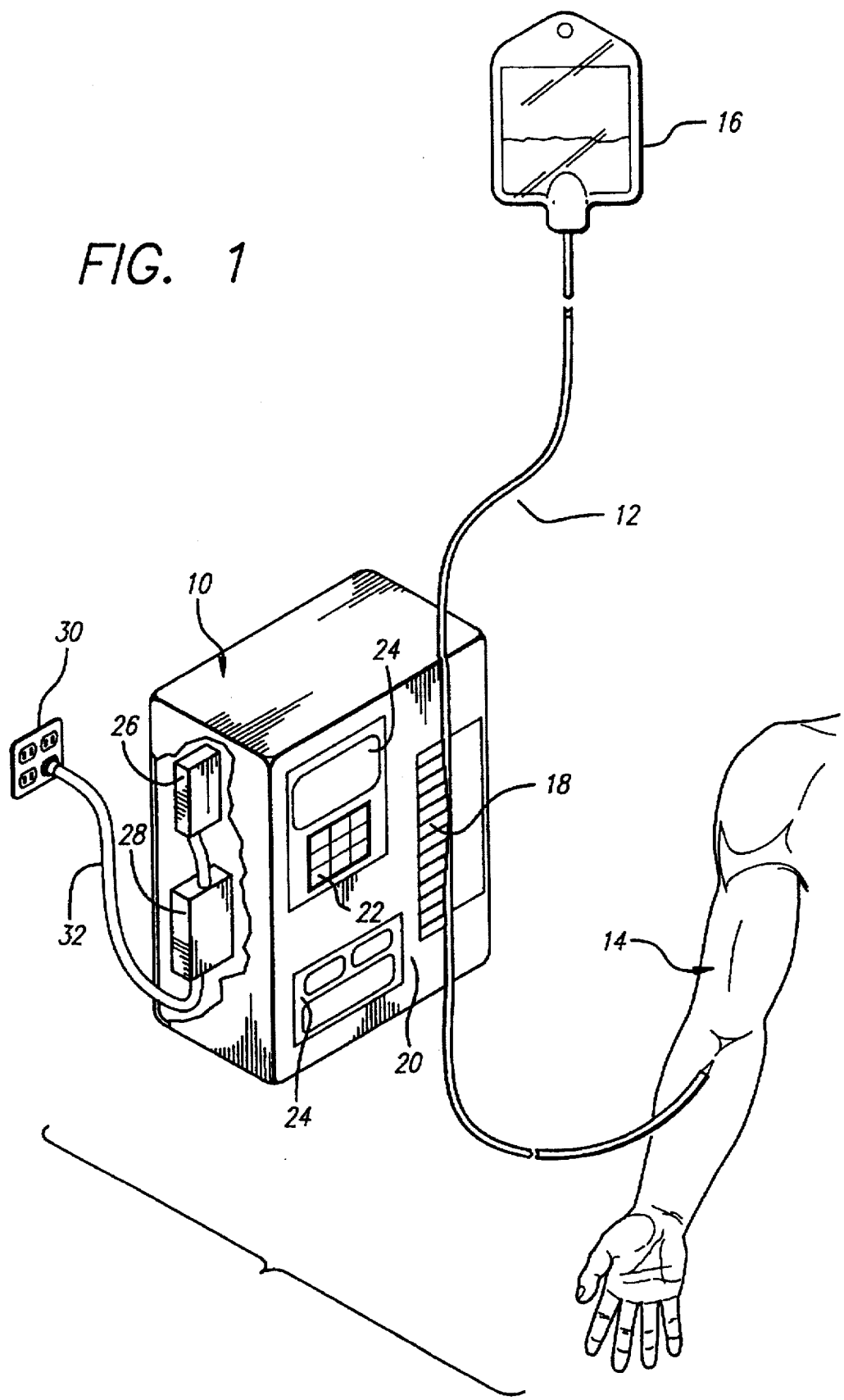
FIG. 1 is a diagrammatical view of a medical infusion pump having a connection to AC wall power, an internal battery, and a power management system in accordance with the invention.

Referring now to the drawings in more detail wherein like reference numerals refer to like or corresponding elements among the several drawings, there is shown in FIG. 1 a medical infusion pump 10 that operates on a fluid line 12 interconnecting a patient 14 and a reservoir of medical fluid 16 to be infused into the patient. The infusion pump includes a drive mechanism 18 that forces fluid from the reservoir to the patient. As one example, the drive mechanism may comprise a linear peristaltic pump and as another example, a syringe-type pump where the syringe comprises the reservoir. Other types of mechanisms may be used. The front panel 20 of the pump includes a keypad 22, and displays 24. Inside the pump, shown in broken-away form, is a battery 26 and a power management system 28, to be described in detail below. The power management system 28 is shown connected to the battery and also to AC wall power 30 through a power cord 32 in this application and controls the pump 10 to operate on this external wall power or on battery power if external power is not available.

Figure 2:
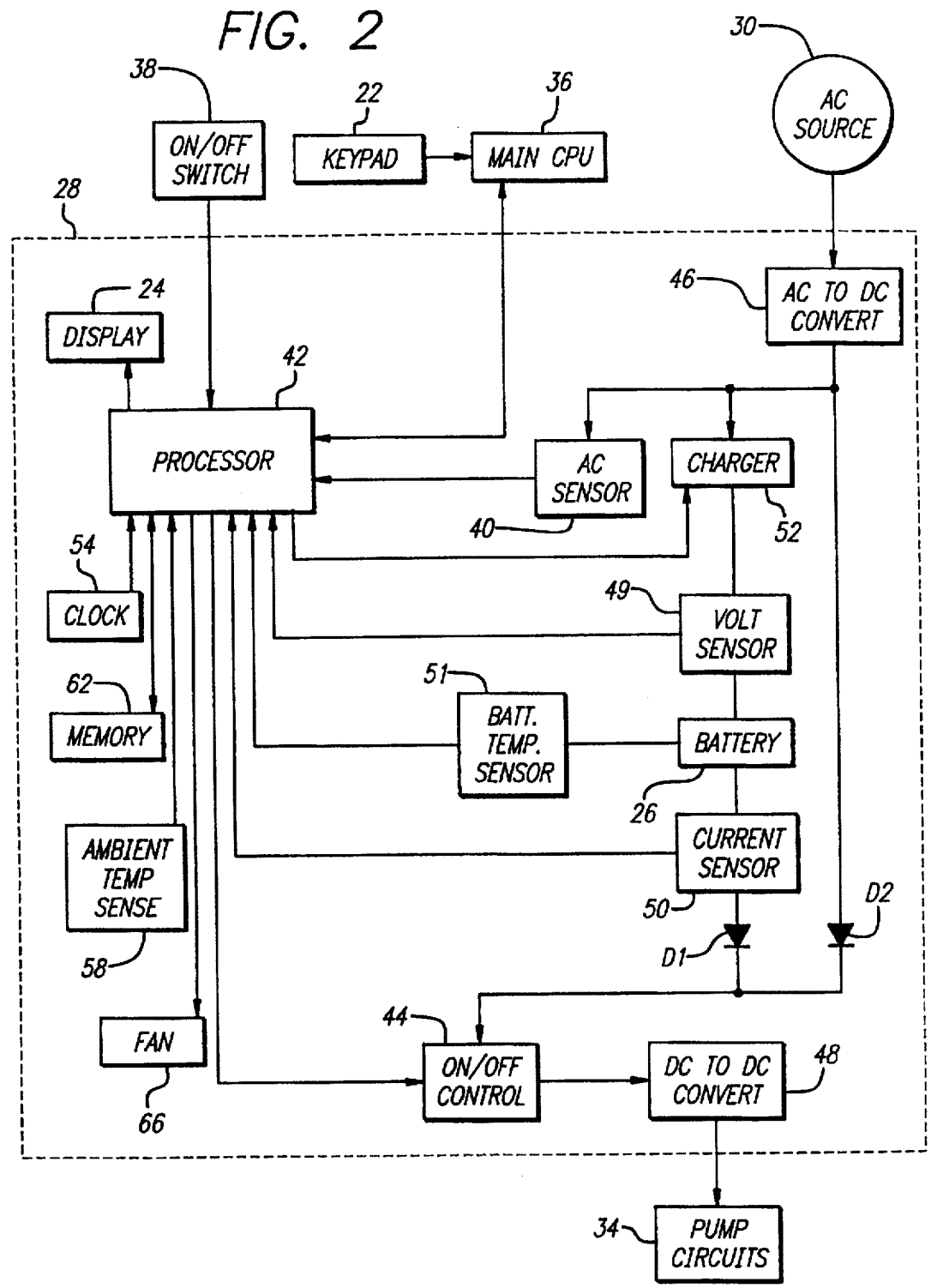
FIG. 2 is a block diagram functionally illustrating elements of a power management system in accordance with principles of the invention.

FIG. 2 comprises a block diagram generally illustrating an embodiment of a power management system 28 in accordance with principles of the invention. In this case, the power management system 28 is incorporated in a biomedical device; i.e., a medical infusion pump 10, and is shown supplying power to the infusion pump circuits 34 from an external AC power source 30. Such infusion pump circuits may include displays, sensors, a motor drive or drives, communication circuitry, and others. The infusion pump also contains a main central processing unit 36 and various other elements including an on/off switch 38, and a keypad 22 to which the power management system 28 is connected.

In the view of FIG. 2, an external power source, in this case an AC power source 30, such as that available from a wall socket unit, provides external power to the management system 28. An AC sensor 40 located in the power management system 28 detects the presence of AC power and provides a detection signal to the power management system processor 42 to indicate that AC power is available. The power management system processor 42 may take many forms but in one embodiment, comprised a Toshiba four-bit CMOS micro-controller having a part number of TMP 47C446. The processor 42 automatically checks the status of the pump on/off switch 38 and if found to be in an "on" status, provides a control signal to the on/off control device 44 to permit the output of the AC-to-DC converter 46 or the battery 26 to be provided to the DC-to-DC converter 48 to power the pump circuits 34. Because the voltage output of the AC-to-DC converter 46 is greater than the voltage output of the battery 26, the diode D1 in series with the internal battery 26 of the power management system 28 will be reverse biased, the diode D2 in series with the AC-to-DC converter 46 will be forward biased and the AC power source 30 alone will provide power to the pump circuits 34.

Although the processor 42 is described here as controlling the power management system, it may have other functions also.

When the processor 42 receives the AC detection signal from the AC sensor 40, it additionally checks the status of the battery 26. Battery charging or deep discharge/recharge operations may be conducted at this time because of the availability of external power, as is discussed below.

In one embodiment, a rechargeable nickel-cadmium battery pack containing ten cells was used as the battery 26. The power management system 28 closely monitors the battery 26 voltage, current, and temperature by means of the battery voltage sensor 49, battery current sensor 50, and battery temperature sensor 51. Such circuits are well known to those skilled in the art and no further details are provided herein. Additionally, the power management system monitors the time during which the battery has been in the power management system, the number of discharge/charge cycles the battery has experienced, and other pertinent factors that may impact the status of the battery. When AC power is available, the power management system will activate the charger 52 to bring the battery to full charge in readiness for possible future battery use to power the pump. Alternatively, depending on certain conditions, the system 28 may subject the battery to a deep discharge/recharge cycle for battery reconditioning purposes, as discussed below.

The charger 52 is controlled by the processor 42 to keep the battery fully charged or to perform a reconditioning deep discharge/recharge procedure on the battery. In the deep discharge operation, the charging circuit 52 will discharge the battery to a predetermined low voltage, above cell reversal voltage. Discharging the battery further may cause cell reversal, permanently damaging the battery. Additionally, the deep discharge voltage value may be set higher if there is the possibility that the voltage of weaker cells may decrease below the cell reversal voltage.

Certain batteries, such as NiCd, can be refreshed and reconditioned by periodic deep discharge cycles. In this embodiment, the processor 42 monitors a system clock 54 and at prescribed intervals, such as every ninety days, causes the charger 52 to perform a deep discharge of the battery 26 and then recharge the battery to fully charged status. Such a reconditioning program can remove a "memory" established in a NiCd battery by repeated partial discharges and recharging. As is well known to those skilled in the art, NiCd batteries typically have unmatched cells. The mismatch between individual cell capacities can lower the overall battery capacity when the battery is subjected to partial discharges and charges. When a battery is partially discharged, then charged for less than the time required to bring each cell to full charge, differences between individual cell capacities result in cells reaching full charge at different times. If the full charge sequence is not then completed, the cell "mismatch" becomes progressively greater. The problem is cumulative in that the mismatch increases for every partial cycle. The result is an apparent lower battery capacity. Shorter run times before complete discharge occur. However, the apparent lowered battery capacity may be removed by performing a deep discharge cycle and then fully charging the battery. The processor 42 at the prescribed interval will perform such an operation automatically to recondition the battery 26.

In one case, a ten cell NiCd battery was deep discharged to approximately 0.9V per cell. In the case of ten cells, the battery voltage at deep discharge will be approximately 9V. After reaching the predetermined discharge voltage level, the battery is then recharged. The battery refresh cycle is initiated at least every ninety days and the charger 52 performs a full discharge and recharge of the battery to condition the battery and maintain battery gauge accuracy. This cycle can occur when the instrument is operating from external power or when the instrument is plugged into external power but is not operating. If the battery is disconnected and reconnected for repair, the refresh cycle will also be automatically initiated by the processor 42. During the automatic refresh cycle, the "E" icon 56 on the front panel of the pump flashes.

Figure 3:
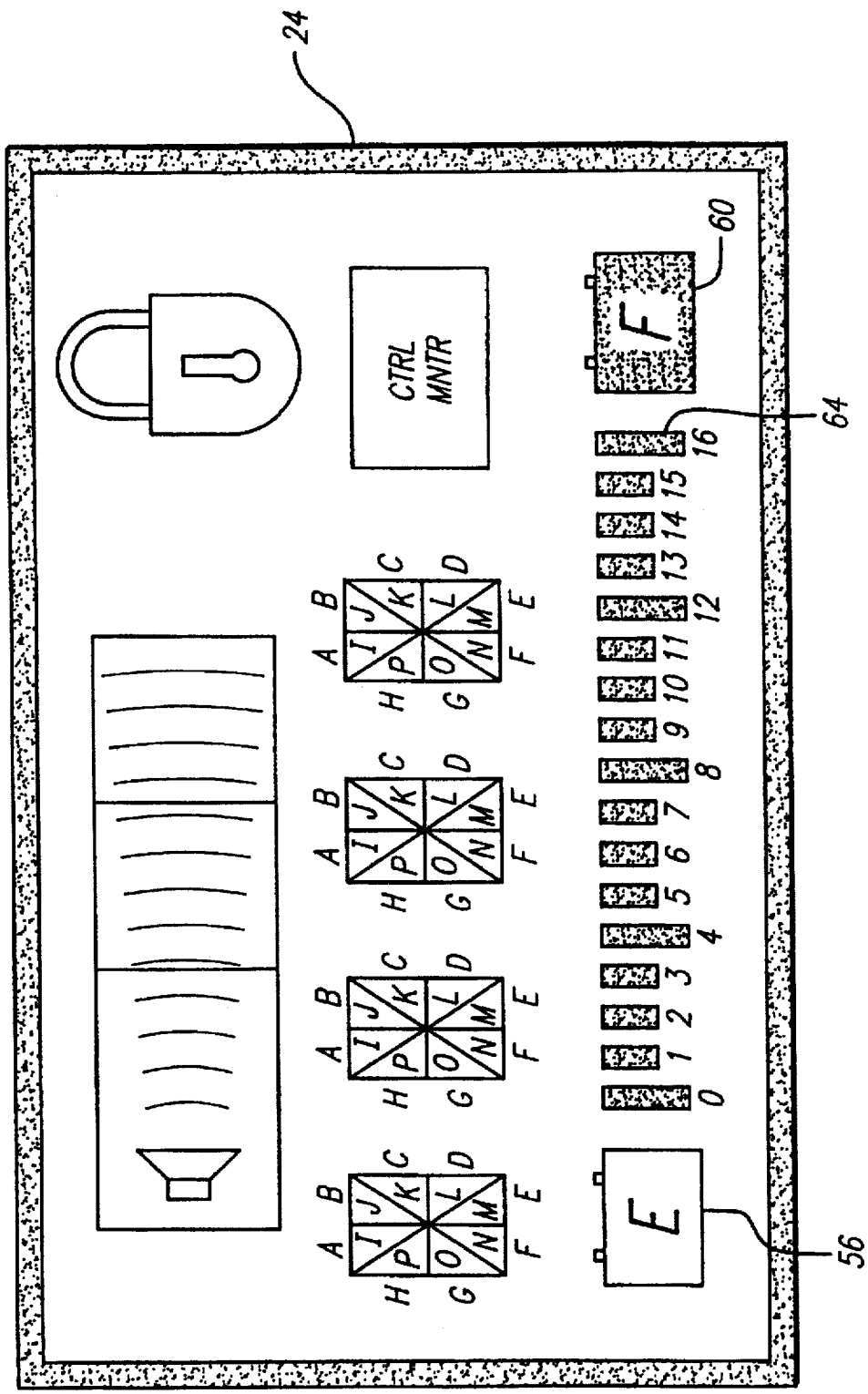
FIG. 3 is an embodiment of a front panel display indicating the run time of the battery, a full charge icon, and a battery empty icon.

In one embodiment, four charging cycles are used. The first is a fast charge cycle that is applied whenever the battery has undergone the deep discharge operation, whenever the battery has been used for more than approximately fifteen minutes, or if the instrument is left off and unplugged for about twenty-four hours. The charge current is one ampere that is turned on and off during instrument operation to limit heat generation. The battery temperature sensor 51 monitors battery temperature. The end of the fast charge is detected when the temperature of the battery rises to five degrees Celsius ("C.") above the ambient temperature as measured by the ambient temperature sensor 58 or when the battery voltage declines by approximately nine millivolts per cell (ninety millivolts total when the battery includes ten cells) below its peak value, or total charge time exceeds four hours. As shown in FIG. 3, an "F" icon 60 indicating full charge exists on the front panel 20 of one embodiment of an infusion pump. This icon will not be illuminated after a fast charge cycle.

The fast charge cycle is used to bring the battery back up to a charged status by applying charge to the battery at a rate that exceeds the manufacturer's recommended charge rate. In some cases, the manufacturer's ideal charge rate would require fifteen hours for the battery to reach a fully charged status, which is undesirable from a user's perspective. By use of the fast charge cycle, ninety to ninety-five percent of the battery's capacity may be provided in as little as two hours. However, because a larger amount of charge is being introduced to the battery in a relatively short time, that time period must be limited and the battery temperature monitored or permanent battery damage will result. The fast charge cycle is therefore characterized by the application of a higher rate of charge that will cause battery damage unless limited in time. On the other hand, the manufacturer's recommended charge rate typically will not cause battery damage, even if applied for an extended period.

After the fast charge cycle has been completed, the processor 42 controls the charger 52 to begin the second charge cycle; i.e., the top-up charge cycle. The top-up charge cycle finishes adding the last few percent of charge to the battery. This cycle should then equalize the weak cells with the stronger cells so that all cells contain the same amount of charge, thus reducing the NiCd memory problem discussed above. As the cells receive further charge from the top-up cycle, the strong cells already are full and will dissipate the overcharge as heat while additional charge is accepted by the weak cells thereby increasing their charge and bringing them up to the level of the strong cells thus equalizing all cells. This cycle charges, in this embodiment, at the manufacturer's recommended average rate of C/10 where C=battery rated capacity in AH (nominally 160 mA) for 180 minutes. The processor 42 controls the duty cycle of the charger. As in the fast charge cycle, the battery temperature is monitored and the processor will turn off the charger 52 if the battery temperature reaches 36° C. The processor 42 waits for the battery to cool down below 32° C. and then applies the top-up charge again. If total time exceeds five hours, the processor will control the charger 52 to go to the float charge cycle. At the completion of the top-up charge cycle, the full icon on the display will be illuminated.

The third cycle is the float charge cycle and it begins at the end of the top-up cycle and maintains full charge in the battery. This charge cycle compensates for loss of charge due to self discharge and maintains the battery continuously at full charge as long as the power management system 28 has a source of external power 30 available. This cycle charges in this embodiment at an average rate of C/50 (nominally 40 mA). The "F" icon 60 (FIG. 3) is illuminated in this mode.

A further battery charge mode is the "hot charge" cycle. When the ambient temperature exceeds a certain level, such as 27° C., the hot charge mode will charge at an average rate of C/10 (nominally 160 mA) in one embodiment for a total charge time of fifteen hours. If the battery temperature exceeds 43° C., the processor 42 turns the charger 52 off until the battery temperature falls below 43° C. Once the charge cycle is complete, the charger switches to the float charge mode.

The ambient temperature sensor 58 measures the ambient temperature surrounding the battery 26. The processor 42 prevents the charger 52 from charging the battery 26 unless the temperature signal from the temperature sensor 58 indicates that the ambient temperature is below a predetermined upper threshold. This upper threshold may vary depending on the charge cycle.

The processor 42 continuously monitors for open circuit conditions in the battery 26 whenever an external power supply 30 is attached. If the battery voltage as monitored by the battery voltage sensor 49 is too high, an alarm signal indicating an open circuit condition for the battery is given. An excessive voltage would likely be a voltage equal to the charger voltage. A sample rate of five seconds can be used to determine the existence of an open condition for the battery 26.

As discussed previously, it is desirable to indicate to the pump operator the amount of time that the battery can run the pump before the battery becomes discharged. A determination of the run time of the battery is based on the amount of charge remaining in the battery and the present current draw from the battery. Current draw may be measured in at least two ways. As a first example, the actual current leaving the battery can be directly measured by an electrical circuit well known to those skilled in the art. The battery current sensor 50 is such a circuit and provides a signal to the processor representative of the current drawn from the battery 26. This level of current draw may then be used to determine the run time.

Another technique for measuring the current drawn from the battery is to store known current draws for each operation mode or infusion rate selected on the infusion pump. These predetermined current draws can be formulated from actual tests and measurements and then stored in the memory 62. The processor 42 may receive the infusion rate selected by the pump operator from the main central processing unit ("CPU") 36 via serial connection, access the current draw corresponding to that infusion rate stored in the memory 62, and apply that current draw in determining the run time.

Determining the amount of charge existing in a battery may be performed in multiple ways also. In one technique, the amount of charge actually applied to the battery to bring it to full charge after a deep discharge cycle (empty battery) may be used as the amount of charge existing in the battery. In this case, the current flowing into the battery during a charging cycle is monitored.

Another method of determining the amount of charge in a battery is to start with the manufacturer's specified or rated capacity, such as 1800 mAH (milli-ampere-hours), determine the amount of charge drawn from the battery during battery usage in accordance with one of the methods discussed above, and subtract the amount of charge drawn from the specified capacity. However, certain batteries, such as NiCd, lose capacity for reasons other than usage, and those losses must also be considered. Some examples are aging and the number of recharge cycles experienced. To give the processor a basis for determining the run time remaining in the battery, the manufacturer's specified capacity, or a lesser amount, may be entered into the processor through an entry device such as the keypad 22. Other means for entering the capacity may include a bar code reader, should the battery have a suitable bar code attached. The processor stores this initial capacity number in memory 62 for use by the processor in determining run time. In another embodiment, the processor may use a default capacity and unless changed by external input, the installed battery will have this capacity in processor calculations. Then when the battery is fully charged, the processor will assign the battery capacity as the amount of charge presently in the battery.

The processor 42 will then display the run time based on the calculated amount of charge stored in the battery and the present current draw from the battery. For example, if the battery is new with a capacity of 1300 mAH and is fully charged, the processor may display a run time of 5.2 hours when an infusion rate of 125 ml/hr is selected for the pump. It is estimated that the current draw at this infusion rate is approximately 250 mA. However if the infusion rate selected is 888 ml/hr, the current draw is estimated at 350 mA and the run time will be displayed as 3.71 hrs. In one embodiment, a default infusion rate of 125 ml/hr is assumed by the processor when an infusion is not occurring, such as when the pump is in a hold mode or the instrument is off. A liquid crystal display 24 may be used to display the run time, the full icon 60, and the empty icon 56. A display layout 24 is shown in FIG. 3 and will be discussed below.

In one embodiment, the processor 42 stores the capacity for the battery 26 that was entered via the keypad 22 in memory 62. The memory 62 also contains various battery-specific rates, such as the rate of capacity decrease due to aging, the rate of charge decrease due to self-discharge, and others. As the processor monitors the system clock 54, it updates the capacity of the battery based on the elapsed time and based on the stored rates that are specific to a change in battery capacity. For example, after a certain time period, the processor lowers the stored number representative of the battery capacity based on this "aging" of the battery.

As the processor monitors the system clock 54, it updates the stored number representative of the charge in the battery based on the elapsed time and based on the stored rates that are specific to a change in battery charge. For example, after a certain time period, the processor lowers the stored number representative of the battery charge based on this self discharge of the battery.

In a particular embodiment, the processor stores a number for the amount of charge existing in the battery as equal to the present battery capacity after a complete charge cycle. As usage, self discharge and other charge affecting events occur, the processor 42 decreases the number representative of the stored charge in the memory 62.

To provide a more accurate display of run time where a NiCd battery is used as the battery 26, certain battery characteristics become important. As discussed in the background section, NiCd batteries lose capacity and charge based on aging and self-discharge. In recognition of these characteristics, the processor 42 automatically reduces the numbers stored in memory representative of the battery's capacity and charge based on time.

Rechargeable batteries such as NiCds steadily lose charge when not in use due to a self-discharge property. The self-discharge rate of the battery, which is in some cases provided by the manufacturer, is also stored in the memory 62 for use by the processor 42. The clock 54 is monitored by the processor 42 to determine the period that the battery 26 has been idle (including no floating charge), the memory accessed for the self-discharge rate for this battery, and the amount of charge stored in the memory for this battery is decremented accordingly. In one case, the amount of charge in the battery is decremented by fifty amp-seconds for every hour of idle time to account for the self-discharge effect. At this rate, it will take approximately twenty hours at room temperature before the full icon 60 is extinguished. As the float charge is applied however, the charge lost due to self-discharge is replaced and the full icon will be lighted and the run time increased.

Rechargeable NiCd batteries also lose their charge capacity due to aging. To account for this effect, the processor 42 decrements the capacity of the battery periodically. The time during which the battery 26 has been connected to the system 28 is determined by the processor by reference to the clock 54. The capacity of the battery is decremented by a predetermined amount as given by the battery manufacturer and the adjusted capacity is stored in the memory 62. In one case, the battery capacity is decreased every eighteen hours by a capacity increment of one amp-second. At this rate, it would take approximately six months for any decrement to be noticed on the run-time gauge 64 (FIG. 3). After four years of use, the battery will have a capacity of about 70% of what it was when it was new. This lowered capacity will be reflected in lower run times, even at full charge.

The amount of charge a NiCd battery can store during charging has been noticed to be dependent on the ambient temperature during charging. As the ambient temperature increases, the amount of charge the battery will accept decreases. At an ambient temperature of 35° C., an enclosed battery will temporarily accept only about ninety percent of the charge it would otherwise accept at 23° C. In one embodiment, the processor monitors the ambient temperature from the ambient temperature sensor 58 and decreases the amount of charge stored in the battery at full charge by a predetermined amount. This decrease will result in lower run times. In one case, the amount stored in the battery 26 is automatically decreased by twenty percent when the ambient temperature rises above 35° C. during charging in order to more accurately reflect this temperature effect. This effect does not cause a permanent change in the battery capacity; however, it does restrict the amount of charge a battery can hold, thus it is considered a capacity-affecting characteristic.

Another factor degrading the capacity of a NiCd battery is the number of complete discharge/charge cycles the battery has experienced. In one case, a manufacturer warrants the battery for five-hundred such cycles and it has been found that a degradation of the battery capacity occurs over the life of the battery as discharge/charge cycles are experienced. In one embodiment, the processor 42 would degrade the capacity of the battery 26 by thirty percent for each two-hundred complete discharge/charge cycles.

Another technique found to be usable in more accurately calculating the amount of charge in a NiCd battery and thus the run time of that battery is to lower the specified capacity of the battery dependent on the application. In the case of an infusion pump, it was found that the discharge of the battery when powering the infusion pump was not ideal and therefore the effective capacity of the battery was lower. For example, the capacity of many NiCd batteries is specified based on a constant current discharge, rather than the constant power discharge as one infusion pump required. In the case where the manufacturer specified the battery capacity to be 1800 mAH, it was found more accurate to program the processor 42 for a 1300 mAH battery, an approximate 28% decrease.

Another factor found to affect the amount of charge stored in a NiCd battery is the failure to fully charge the battery. To prevent overestimation of the charge in the battery 26 after a recharge, one embodiment includes a degradation counter implemented in the processor that degrades the amount of charge in the battery by a predetermined amount at the end of a fast charge cycle. After a recharge, the processor 42 typically stores the value of the battery capacity as the value for the amount of charge existing in the battery. However, in one embodiment, the value for the amount of charge the processor calculates to be in the battery is reduced by 3.125% from the service capacity after the fast charge cycle. Then after completing the top-up cycle, the charge calculated by the processor to be in the battery is increased by 6.25% from that previous number, although it cannot exceed the "service capacity" number for the battery. As used herein, the "starting capacity" of a battery is the manufacturer's rated capacity. The "service capacity" is the rated capacity less the effects of age, number of charge/discharge cycles, etc. The "available capacity" is the service capacity less the effects of incomplete charging. Thus, in the case where only the fast charge cycle has been completed, the available capacity of the battery may be rated at the service capacity less 3.125%. After the top-up charge cycle, the available capacity will equal the service capacity, in most cases.

In the case where the battery is new and has not been cycled through discharges and charges, its service capacity is less than the starting capacity. In one embodiment, a service capacity of 90% of starting capacity is assigned to the new battery. Then after a fast charge cycle, the available capacity is reduced by 3.125% from the service capacity, but after the top-up charge cycle, the available capacity is increased by 6.25% which also raises the service capacity by 3.125%. When the battery service capacity equals the starting capacity, the available capacity will not exceed the starting capacity even after the top-up cycle. As is discussed above, the service capacity will be reduced from the starting capacity due to the effects of time and number of discharge/charge cycles completed. The available capacity does not exceed the service capacity when the service capacity has been reduced from the starting capacity for these reasons.

It was found that such a degradation counter was necessary due to the failure to compensate for the NiCd memory effect with only a fast charge cycle. Reducing the calculated charge in the battery as set forth above resulted in a more accurate estimate.

Referring now to FIG. 3 in more detail, a display of run time, full, and empty icons is shown. The bar graph 64 presents run time in fifteen minute increments with zero time at the left and four hours (or sixteen quarter hours) at the right. Run time in excess of four hours is not shown on the bar graph other than that the graph does not decrease during use until there is actually less than four hours run time left. The F icon 60 indicates that the battery is fully charged regardless of the run time shown. The E icon 56 indicates that the battery is completely discharged and flashes when the processor is controlling the charger 52 to perform a deep discharge/recharge cycle on the battery. The other icons and character displays are not pertinent to the power management system.

Indications are given to the user including audible and visual alarms. In one embodiment, when the battery pack of ten cells reaches 12.1 V, a low battery warning indication is provided. When the battery pack reaches 11.45 V, a battery depleted alarm is provided. When the battery pack reaches 10.25 V, power to the instrument motor and control circuits is turned off and a backup alarm indication is activated.

When a battery needs to be removed for maintenance on the pump for example, the processor will retain in memory 62 the last determined capacity of that battery. Unless reprogrammed, the processor will apply this stored capacity to the battery reinserted into the pump after maintenance has been completed. Thus, the battery may be removed at any time without fear that the accuracy will be lost. When a new battery 26 is installed in the pump, the operator will enter into the processor 42 through the keypad 22 its specified capacity (or a reduced capacity as explained above).

The battery voltage sensor 49 continuously monitors the battery voltage and provides a representative signal to the processor 42. Stored in memory 62 is a table indicating the expected voltage for the battery versus the amount of stored charge. Thus if the processor has determined that the battery has a certain stored charge, the table in the memory may be accessed to determine the expected voltage of the battery for that charge. If the actual voltage furnished by the battery voltage sensor 49 is significantly less than that expected voltage, a battery short may be indicated. If the battery voltage drops too soon while operating the pump 10, the processor 42 determines that a short-circuit condition exists for the battery 26, and an alarm is given. In a multiple battery pack, the battery voltage is lowered when two or more battery cells have shorted. Shorted battery cells may only be detected after the battery has been fully charged. For example, if during the operation of the pump 10, the run-time gauge 64 indicates that there are four hours remaining in the life of the battery, yet the battery voltage is only 0.9 volts per cell, the processor 42 determines that a short condition exists.

In summary, there are four factors discussed above that degrade battery capacity. These are:

1. Non-ideal discharge rate
2. Aging of the battery
3. The number of discharge/charge cycles performed
4. Elevated ambient temperature during charging (not permanent)

There are three factors discussed above that lower the amount of charge actually stored in the battery. These are:

1. Failure to complete a charge cycle to full charge all cells (top-up cycle not completed)
2. Self-discharge
3. Use of the battery The power management system 28 provides the interface between the power on/off switch 38 and the main CPU 36. When the infusion pump is off, the receipt of an on signal from the switch 38 causes the processor 42 to apply power to the rest of the infusion pump through the on/off control 44. Once power is on, the main CPU 36 receives switch selections and determines the appropriate response. If the response is to turn power off, the main CPU 36 requests that the power management system 28 remove power from the pump. The power management system then controls the on/off control 44 to the off mode.

Figure 4A:
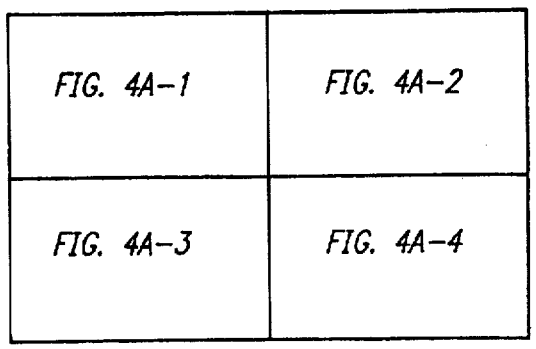
FIGS. 4A through 4D are plan views of the relationship of the various schematic circuit diagrams of FIGS. 4A-1 through 4A-4, 4B-1 through 4B-6, 4C-1 through 4C-5 and 4D-1 through 4D-4 illustrating of an embodiment of a power management system in accordance with the invention.
Figure 4B:
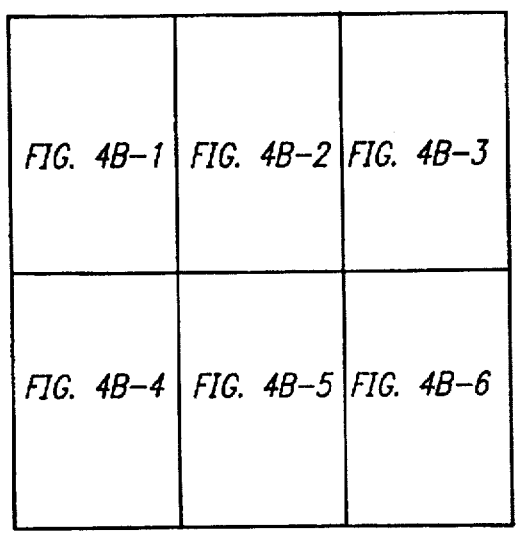
Figure 4C:
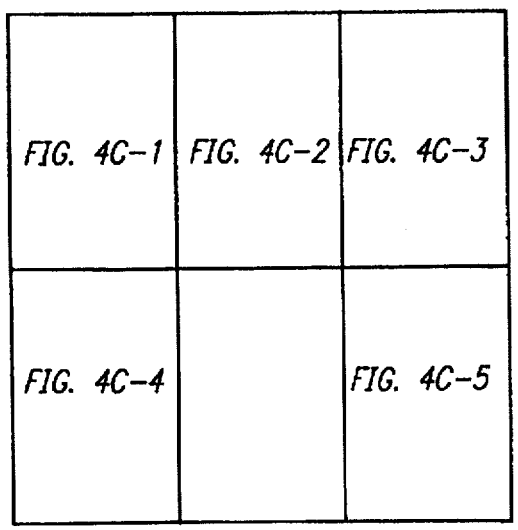

FIGS. 4A, 4B, 4C, and 4D present schematic diagrams of an embodiment of a power management system. Turning now to FIGS. 4A-1 through 4A-4, a battery 26 is shown connected to a charger 52 and a battery voltage monitor 49. The battery 26 includes an internal temperature sensor 51. Their operations are as described above. The power input to the charger is shown as DC_INPUT and is power from the AC power source 30 that has been converted to DC. Also shown is an AC sensor 40 that indicates when AC is available. A system power source selector circuit 100 provides the convened AC to the biomedical device for operation when AC is available by reverse biasing diode CR3. However, when it is desired to discharge the battery 26 for its periodic refresh cycle, the PWR_ON line is activated by the processor 42 (FIGS. 4B-1 through 4B-6) and the battery is used to power the device. The VAO shutdown circuit 102 monitors the battery voltage and will disconnect the battery from the circuit should its voltage reach a predetermined level, such as 9.75 volts as discussed above.

Referring now to FIGS. 4B-1 through 4B-6, the processor 42 is shown and an ambient temperature sensor circuit 58. Referring to FIGS. 4C-1 through 4C-5, a battery refresh cycle load 104 is shown comprising a 47 ohm, 7 watt resistor R273. When the biomedical device is not operating, the processor 42 will control device Q9 to apply the load R273 for discharging the battery 26. As discussed above, the processor 42 will use the instrument to discharge the battery when the instrument is operating.

Figure 4D:
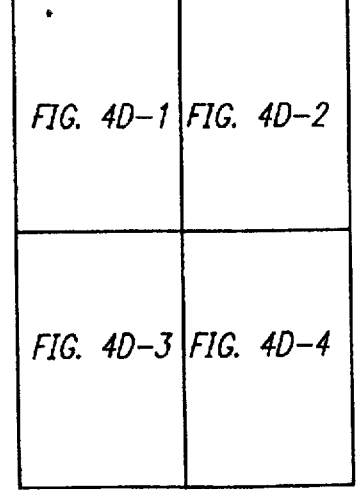
Figures 1, 4A:
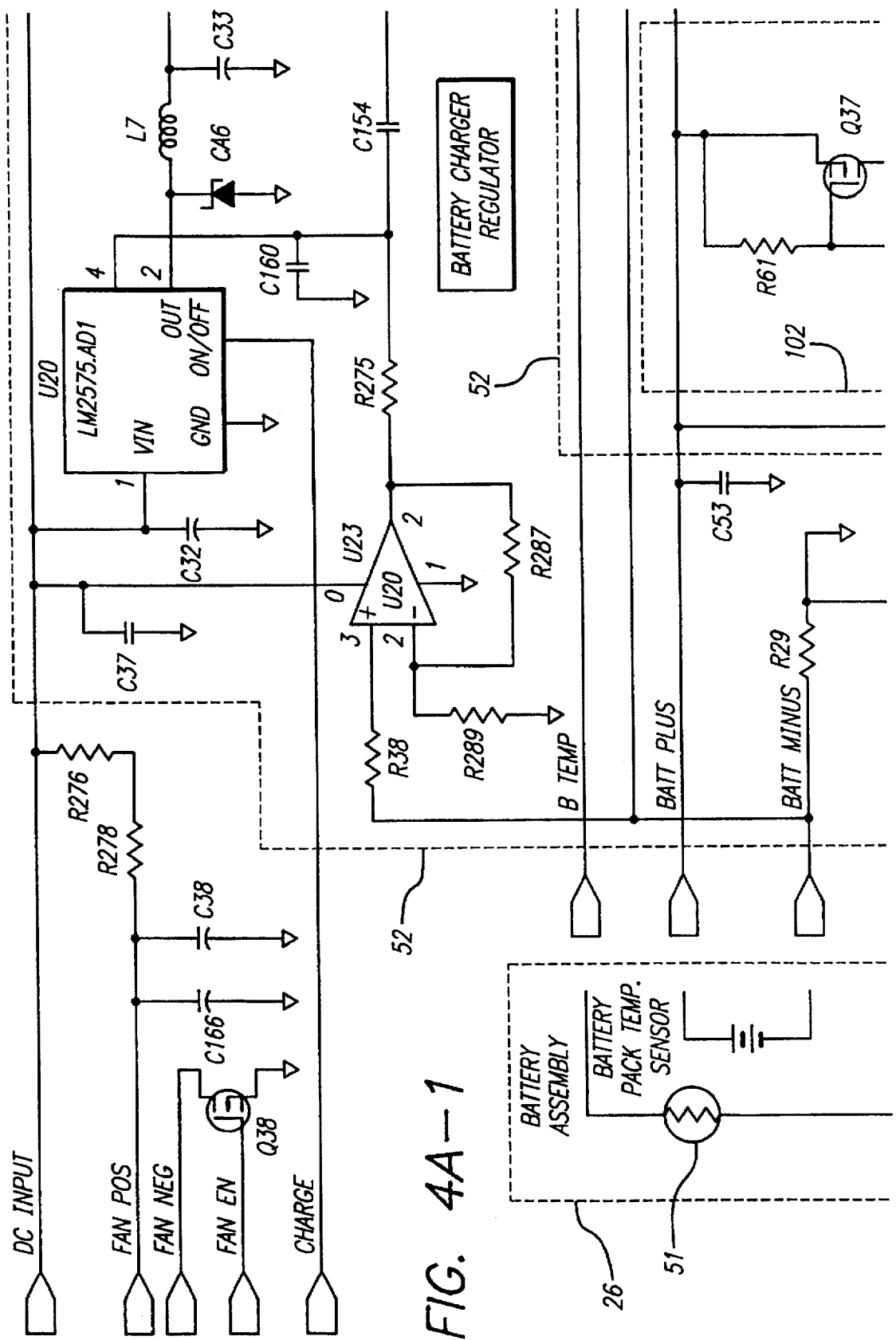
Figures 2, 4A:
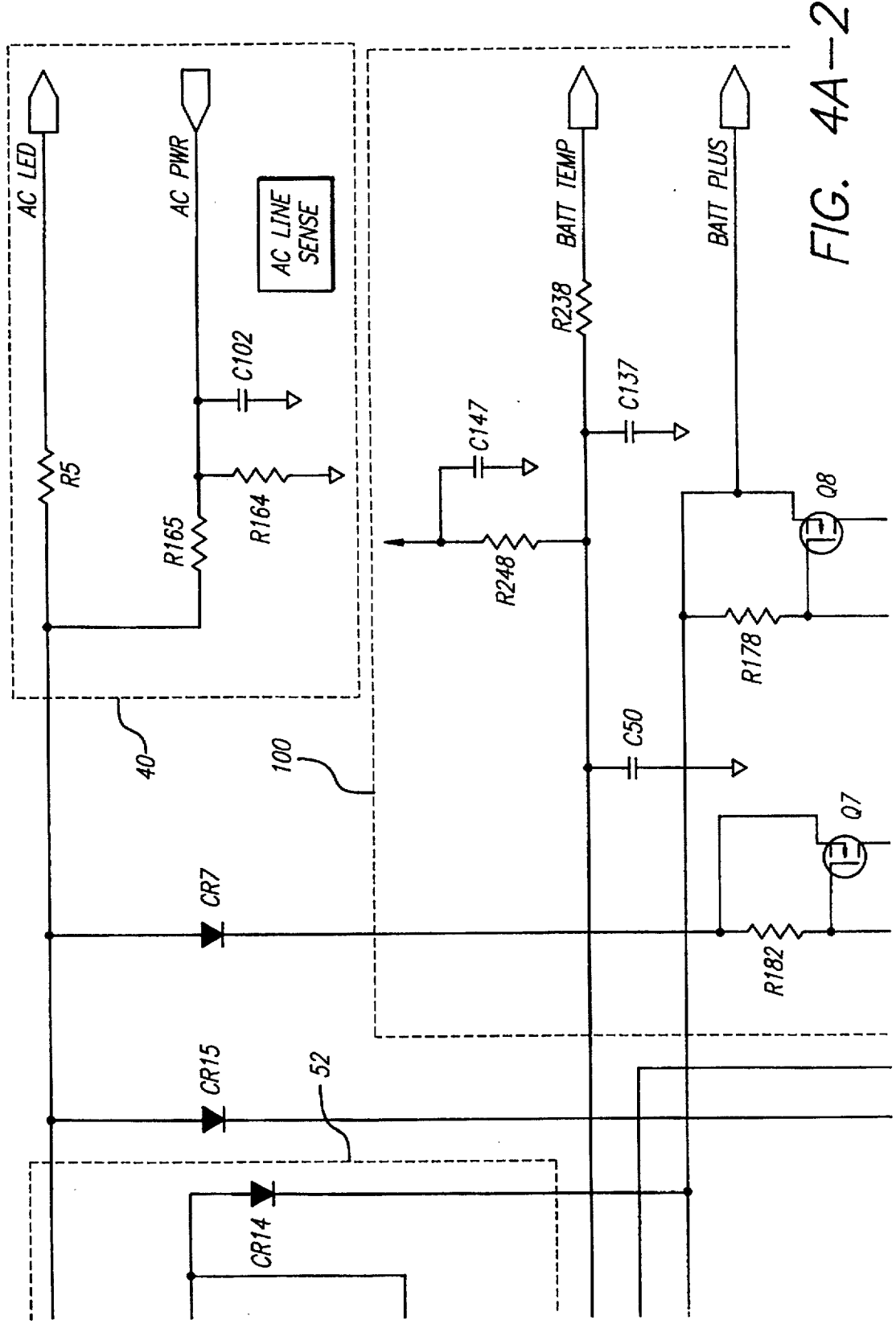
Figures 3, 4A:
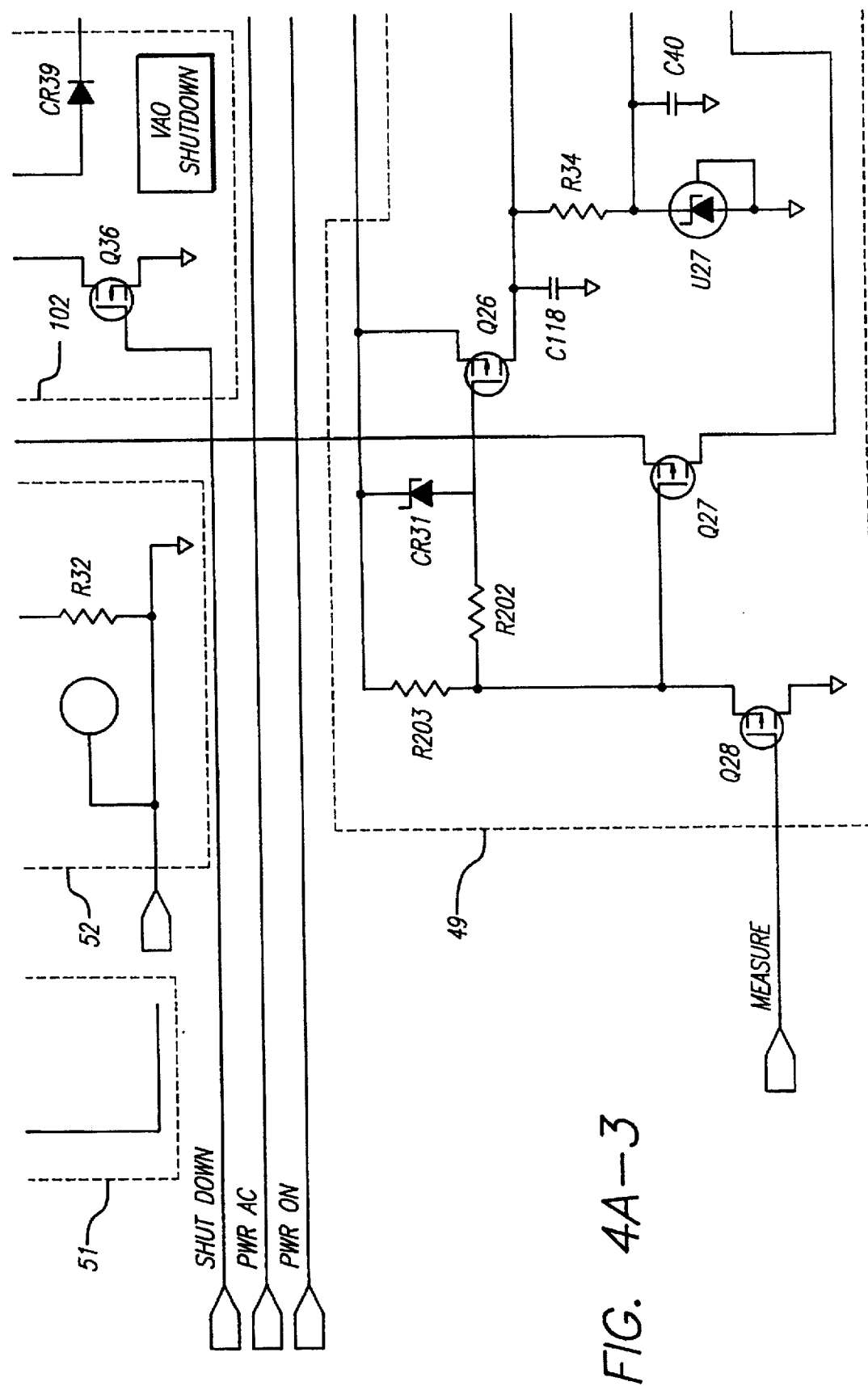
Figures 4, 4A:
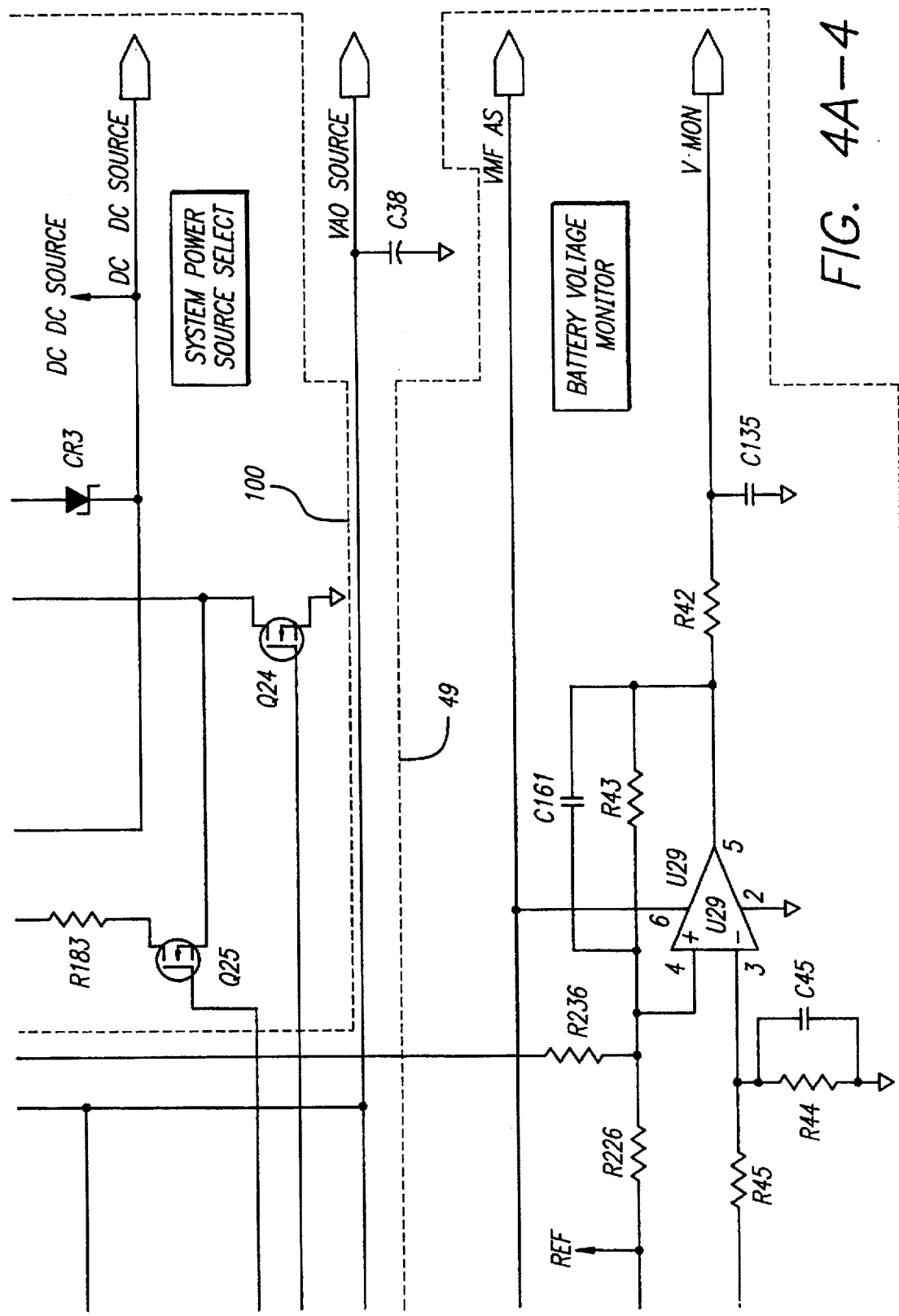
Figures 1, 4B:
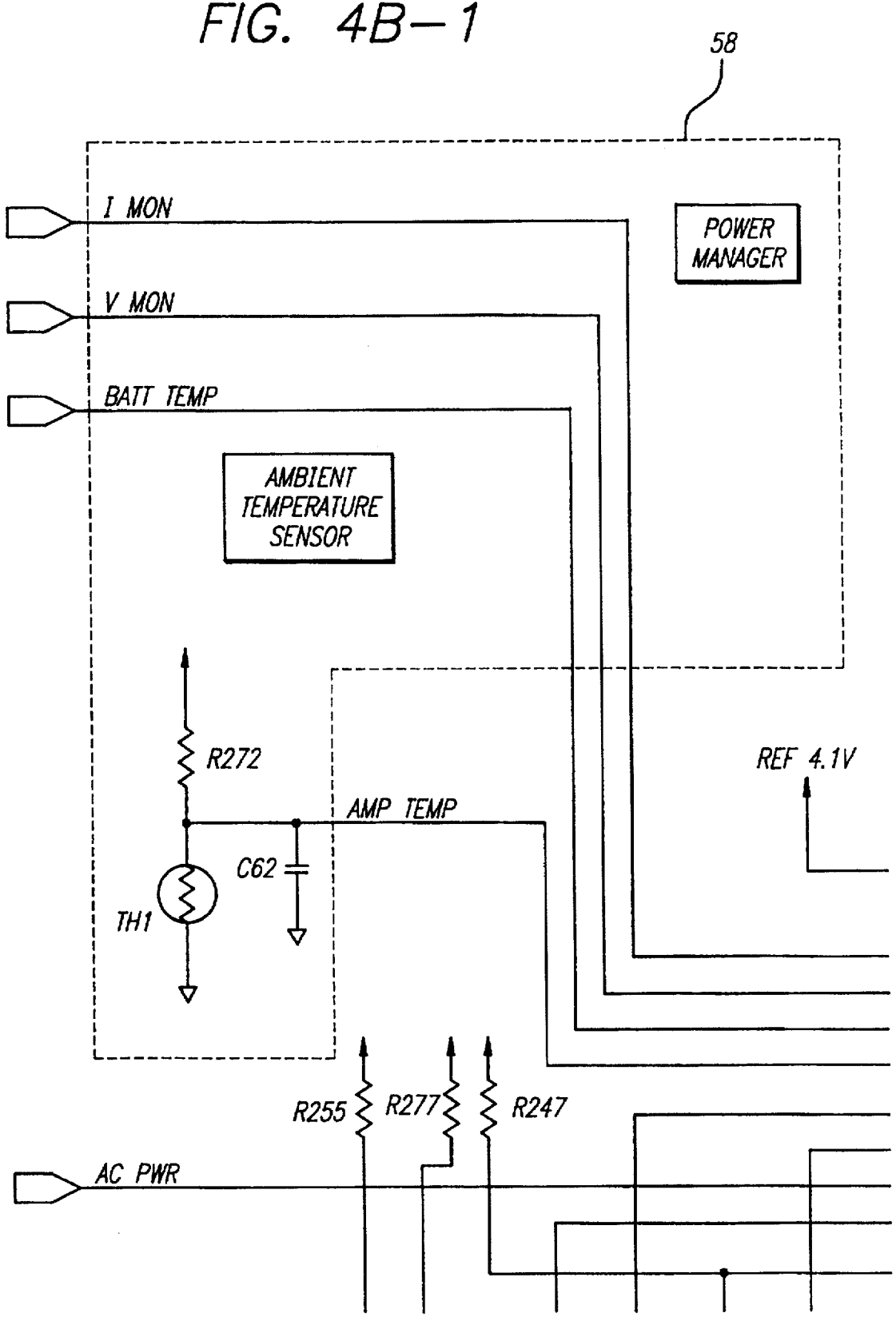
Figures 2, 4B:
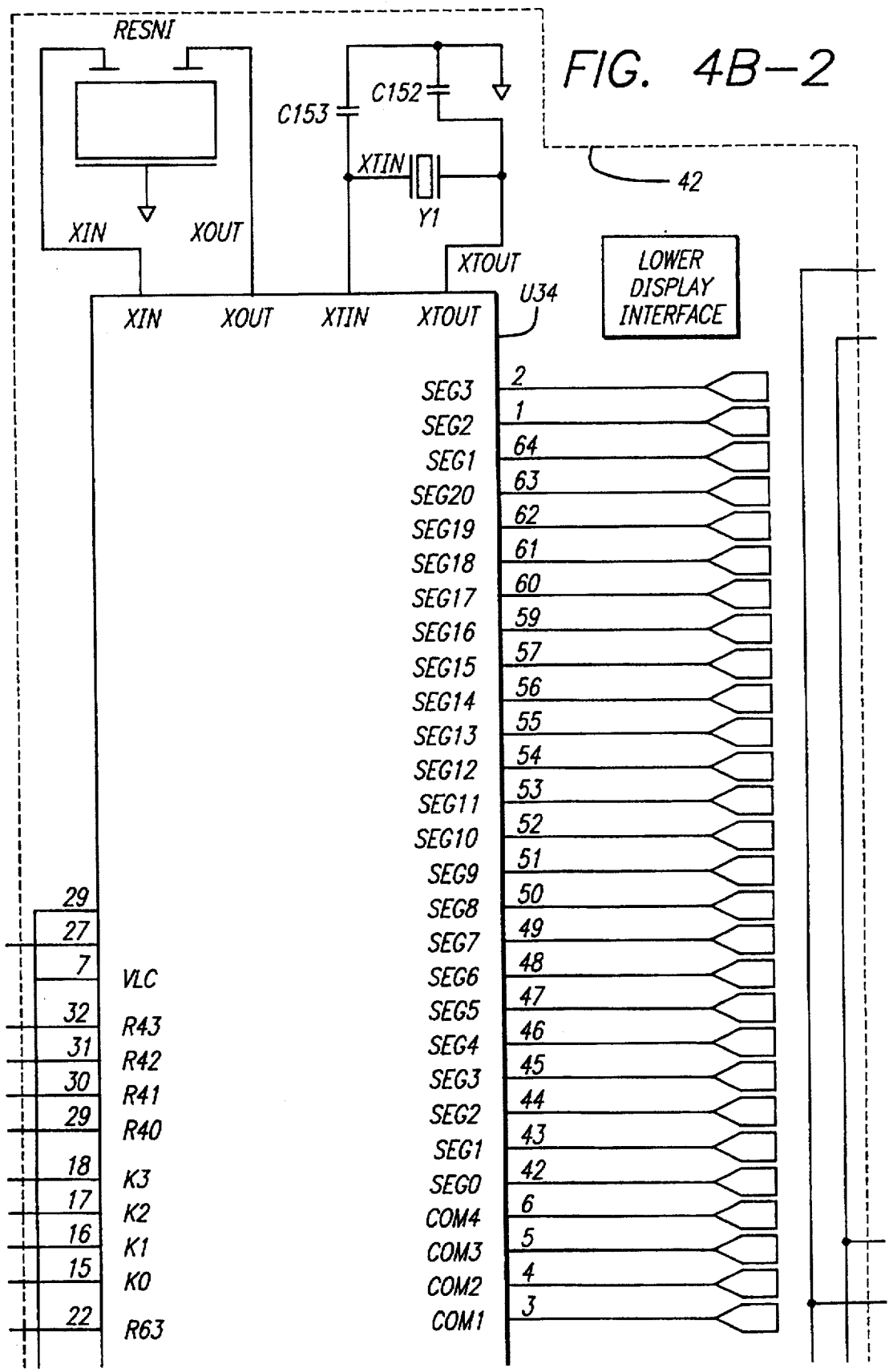
Figures 3, 4B:
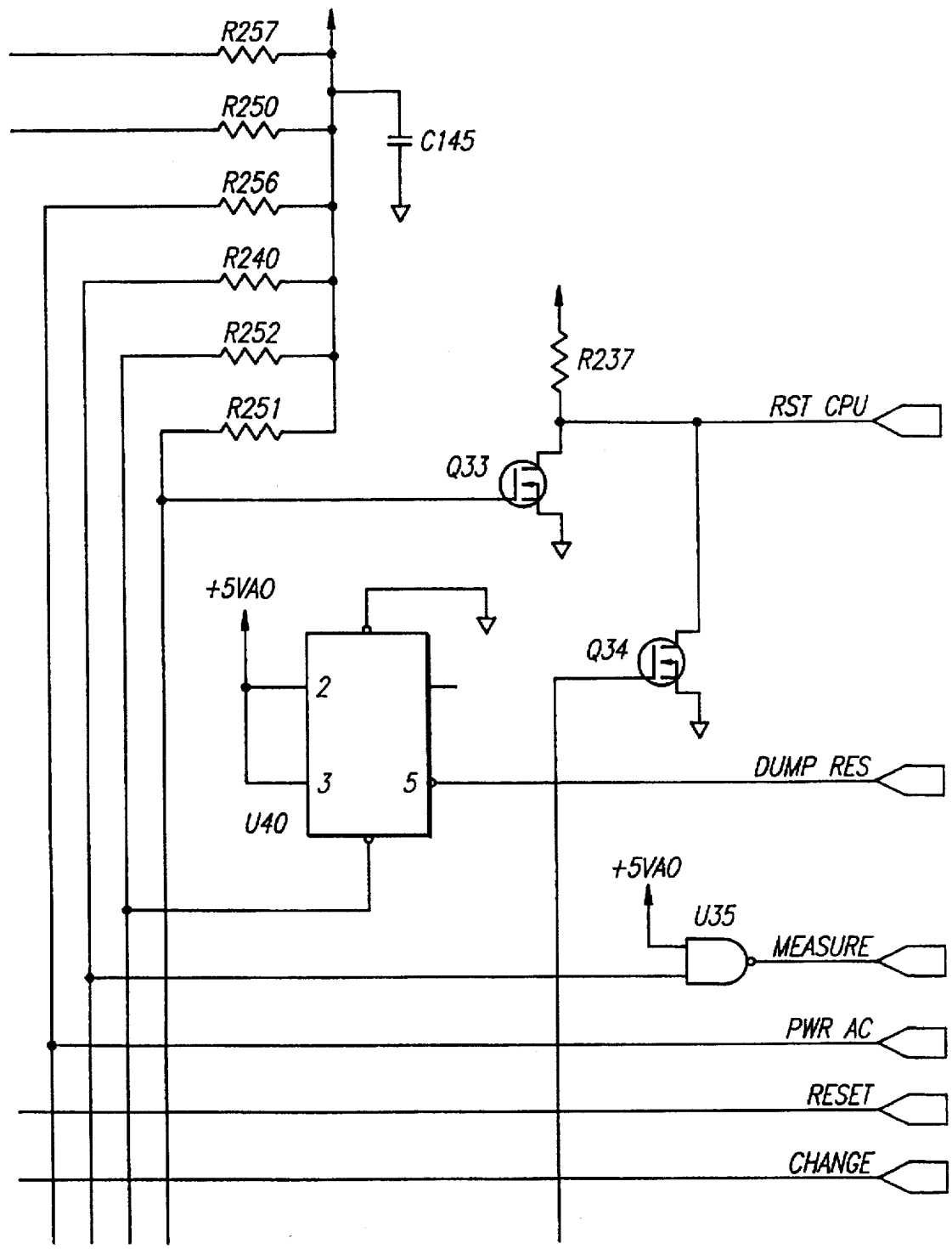
Figures 4, 4B:
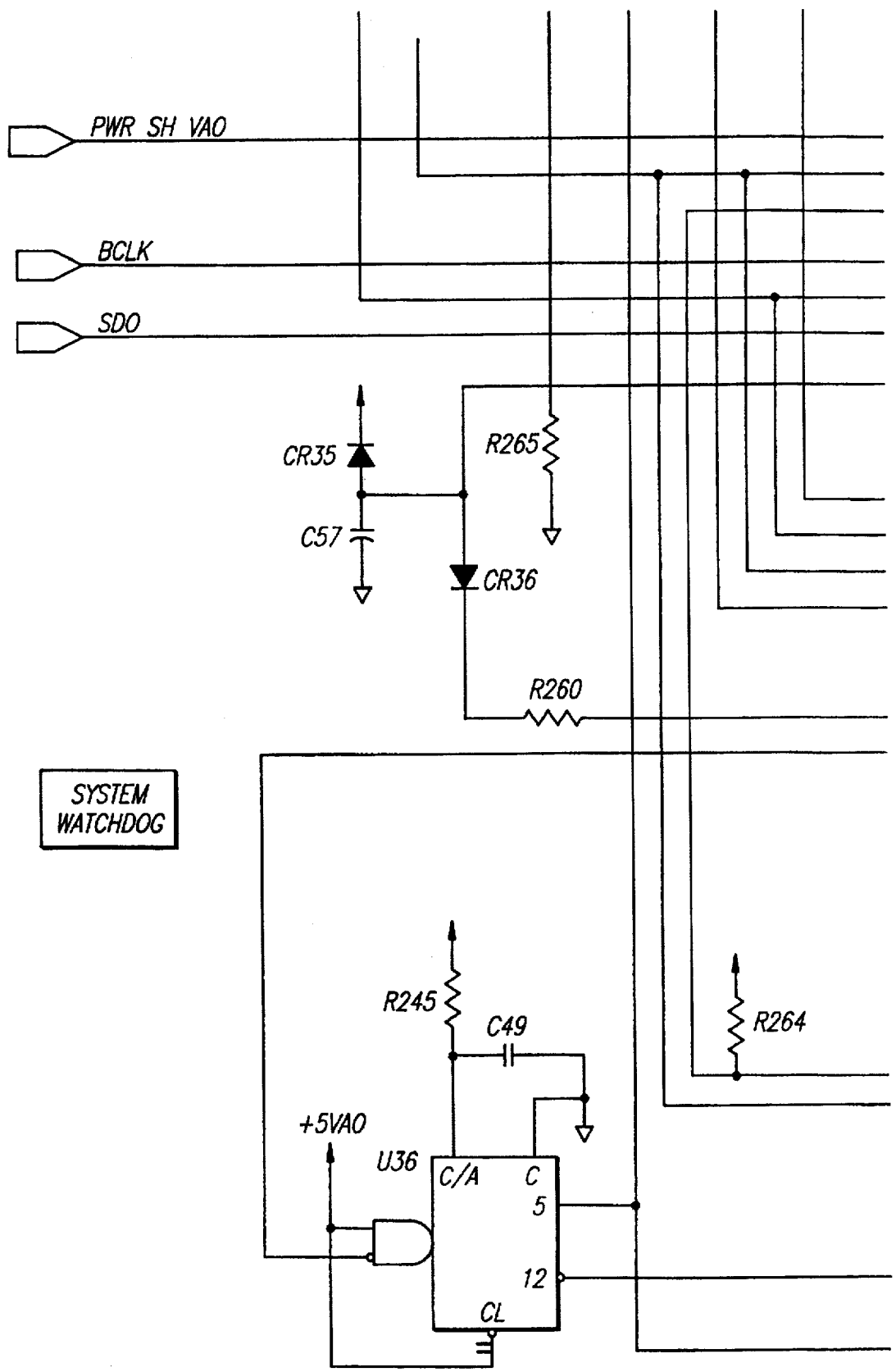

Referring now to FIGS. 4D-1 through 4D-4, the system current monitor 50 is shown. Also, a 5 volt "always on supply" 106 is shown that is powered by the battery via the VAO_SOURCE line. As discussed above, when the battery voltage decreases below a certain level, the battery will be disconnected from the instrument and the 5 volt always on supply will not be powered.

An internal fan 66 is used for cooling, mainly to help prolong battery life and increase charge capacity. In one embodiment, the fan had a rating of 6.3 CFM. The fan is always on when the battery is charging with the fast or top-up cycles. During the float charge cycle, the processor 42 will control the fan to be on at 41° C. and off at 35° C. battery temperature to limit the heat to which the battery is exposed.

Figures 4, 4B, 5:
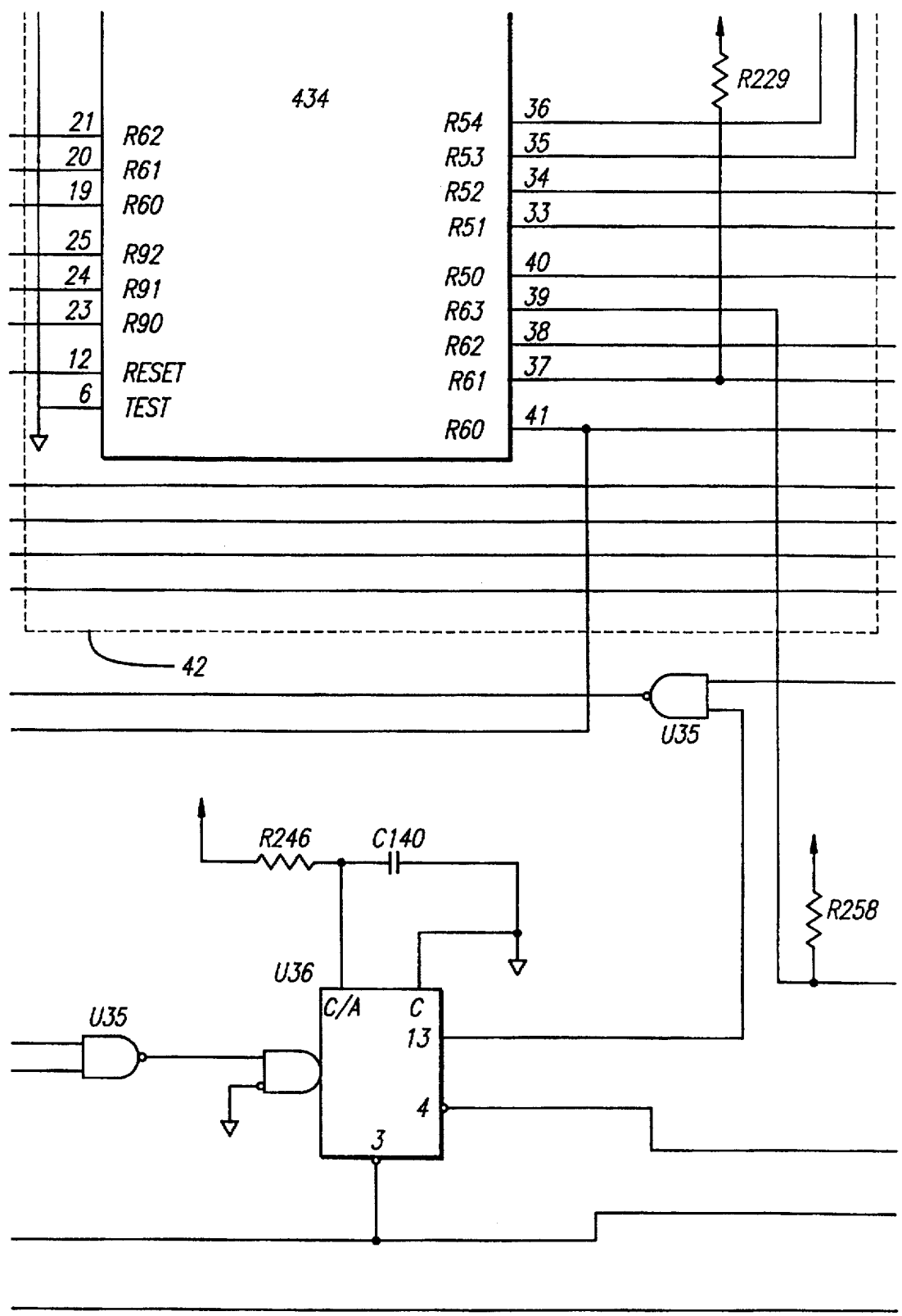
FIG. 5 is a chart illustrating a charging cycle of the power management system in accordance with the invention.
Figures 4, 4B, 5, 6:
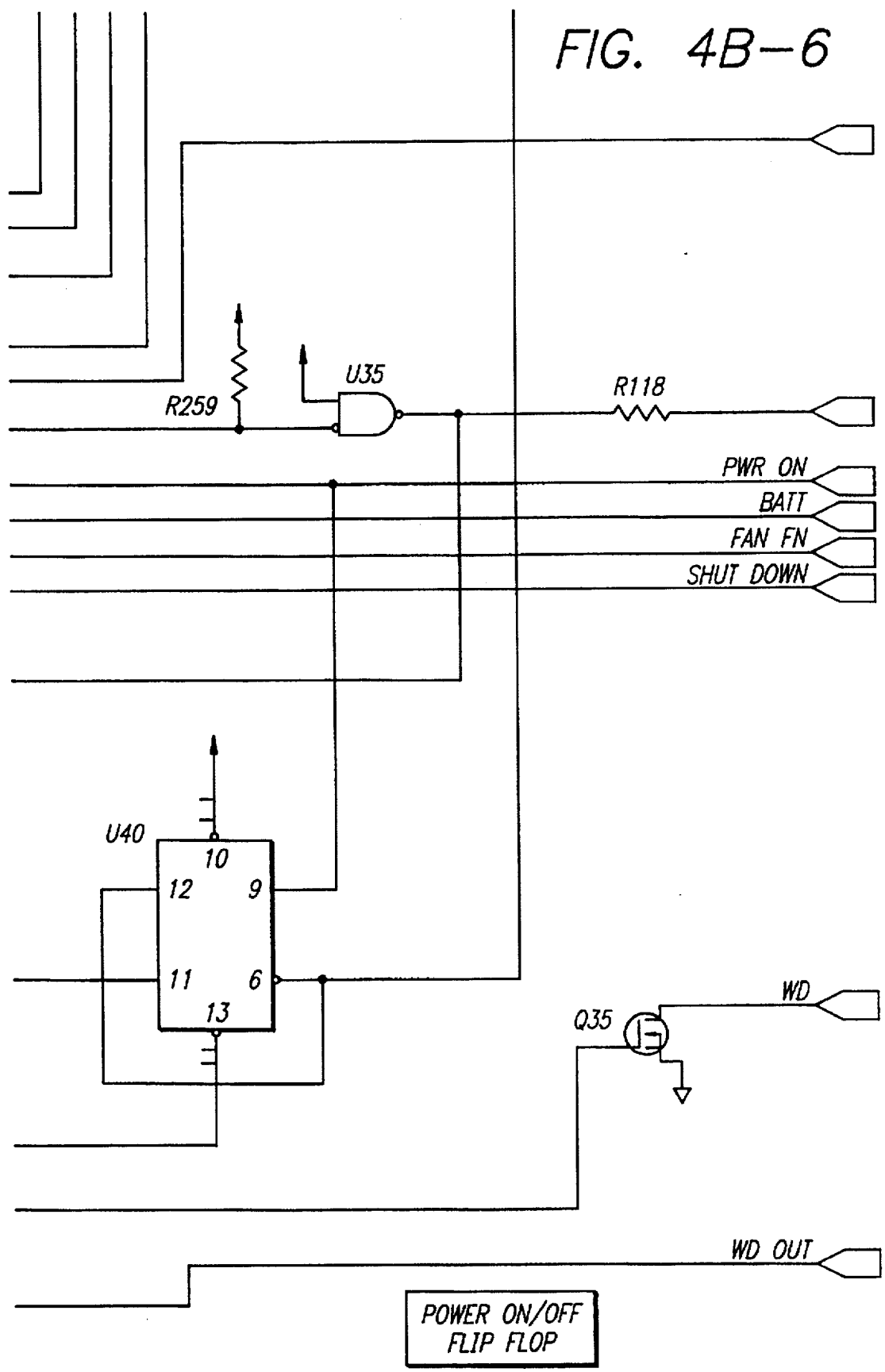
Figures 1, 4C:
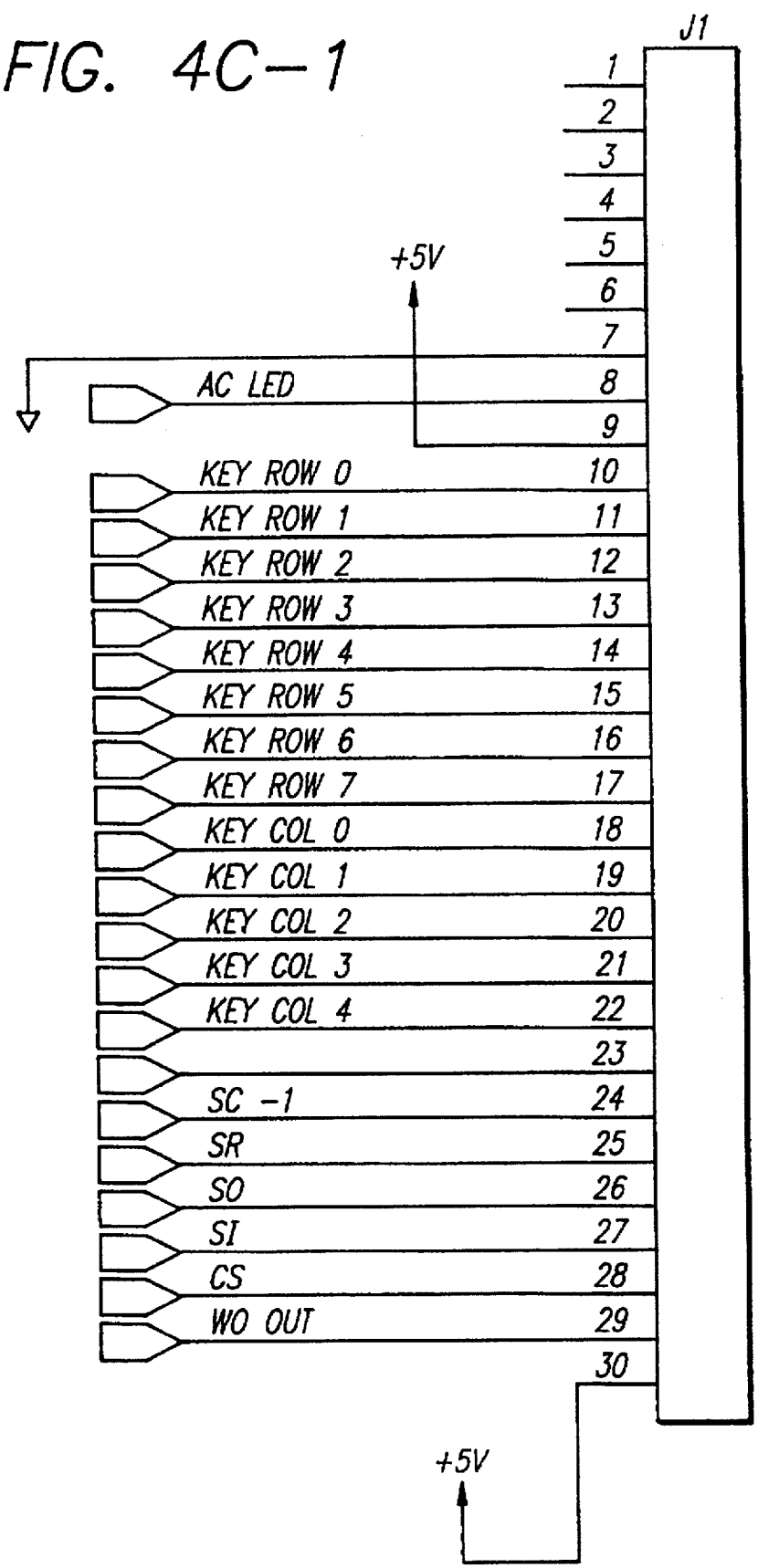
Figures 2, 4C:
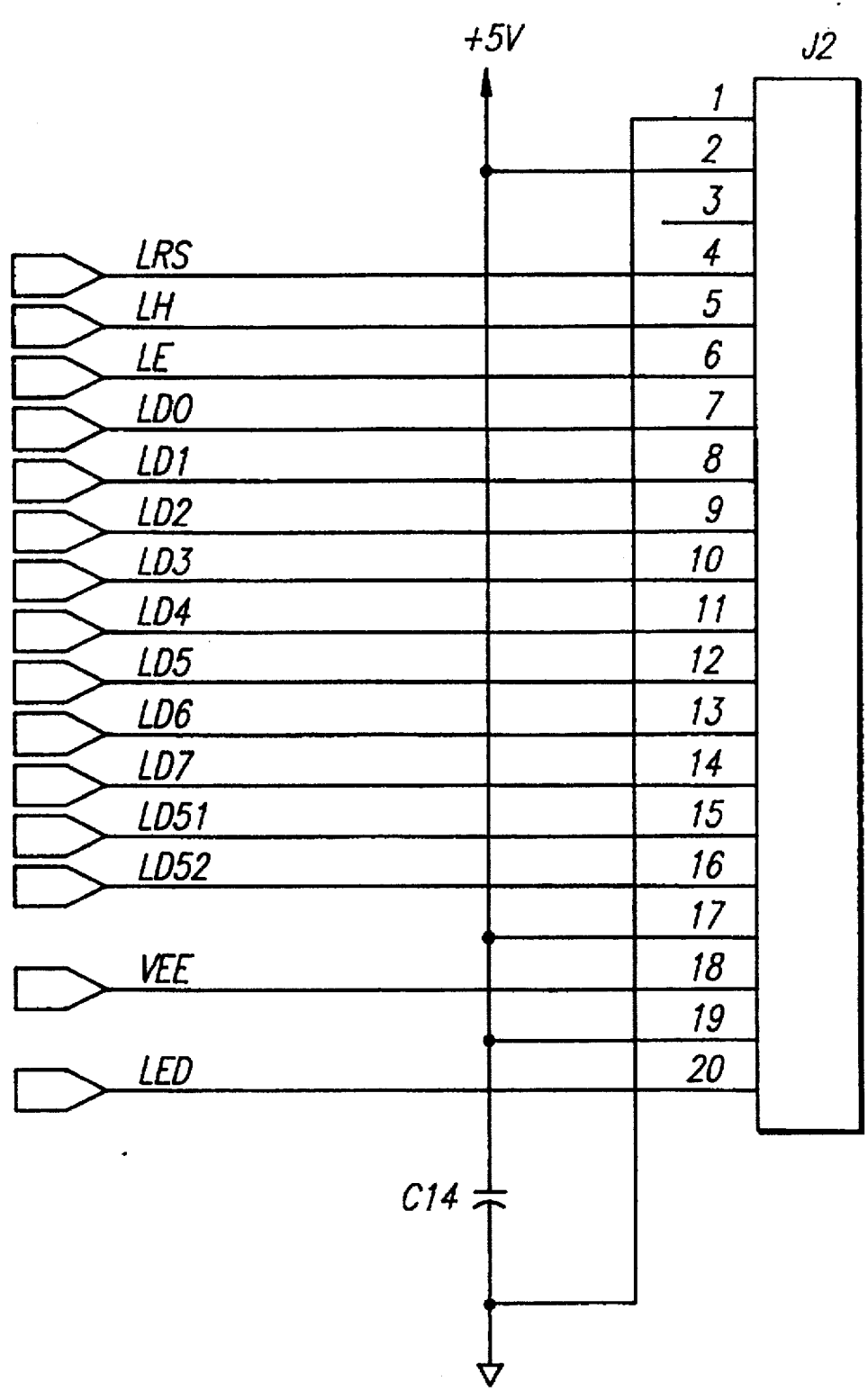
Figures 3, 4C:
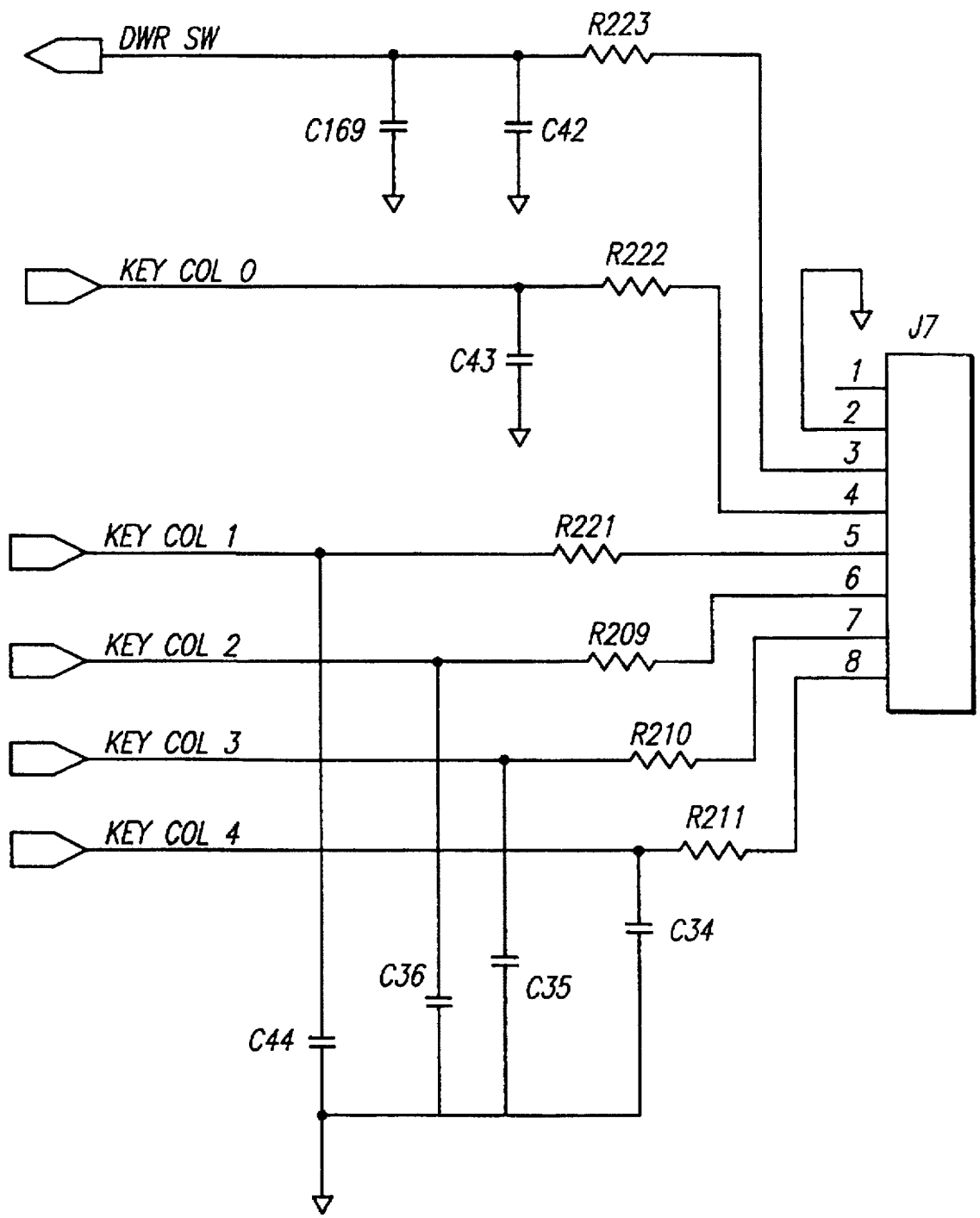
Figures 4, 4C:
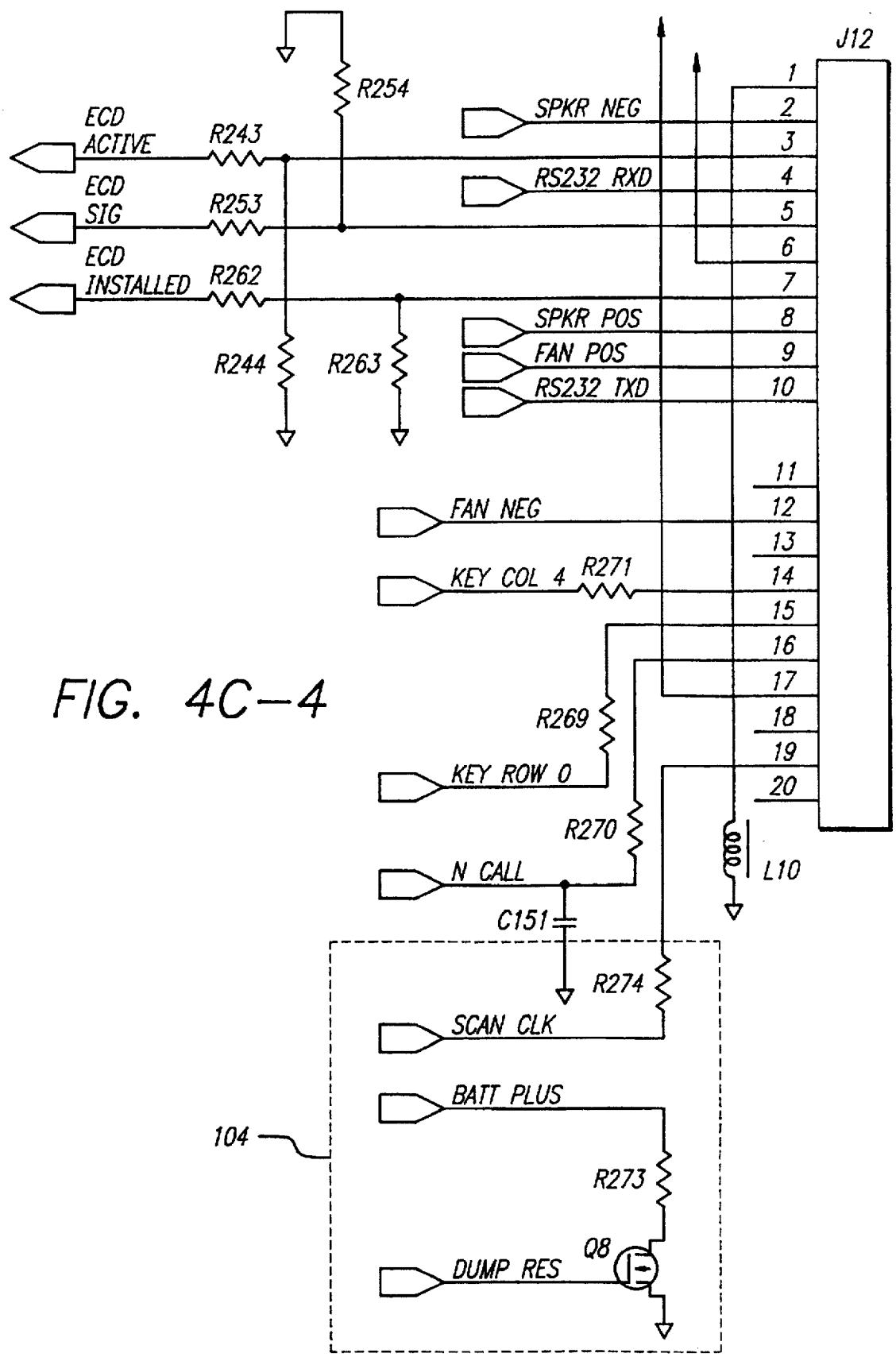
Figures 4, 4C, 5:
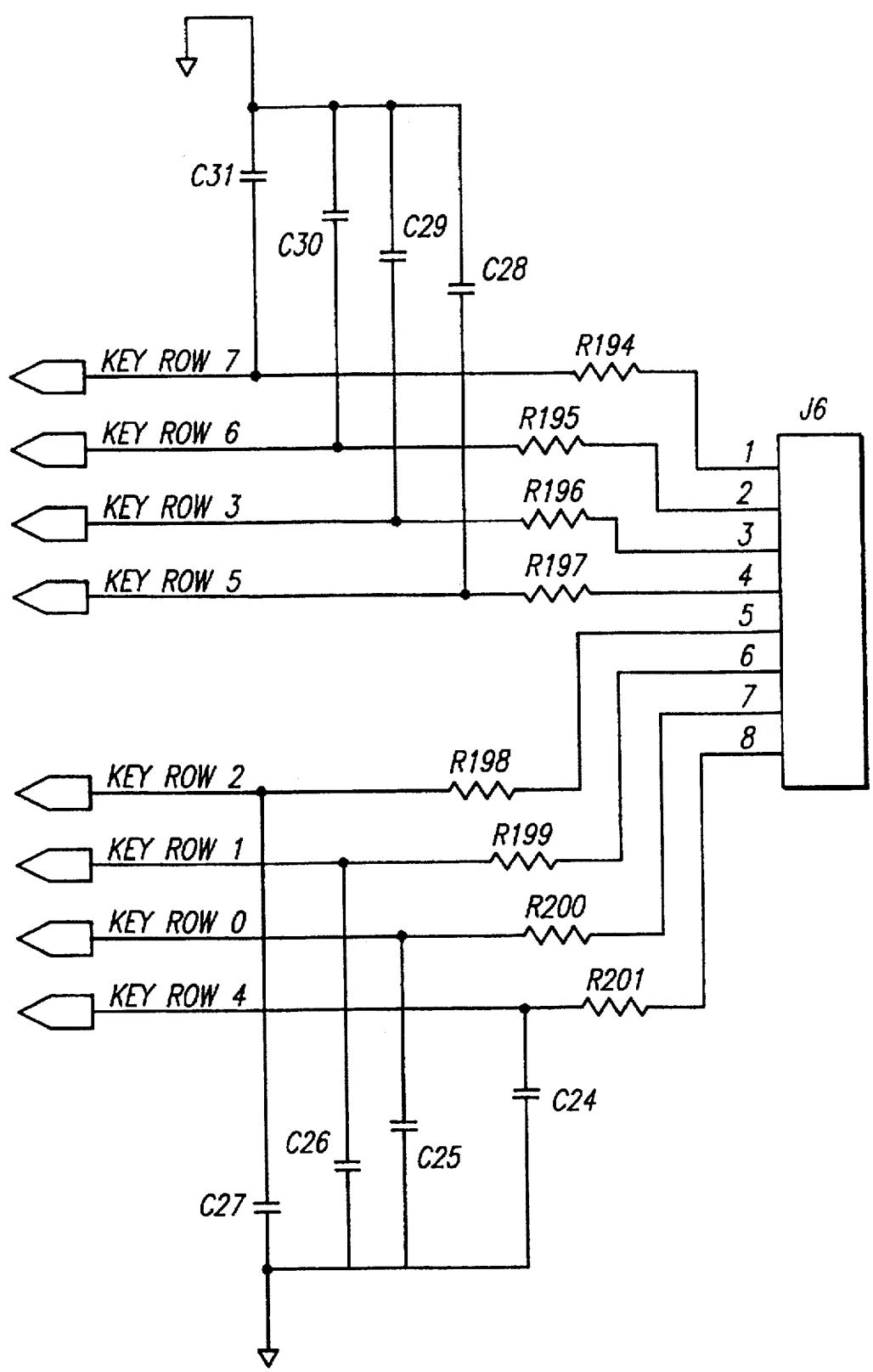
Figures 1, 4D:
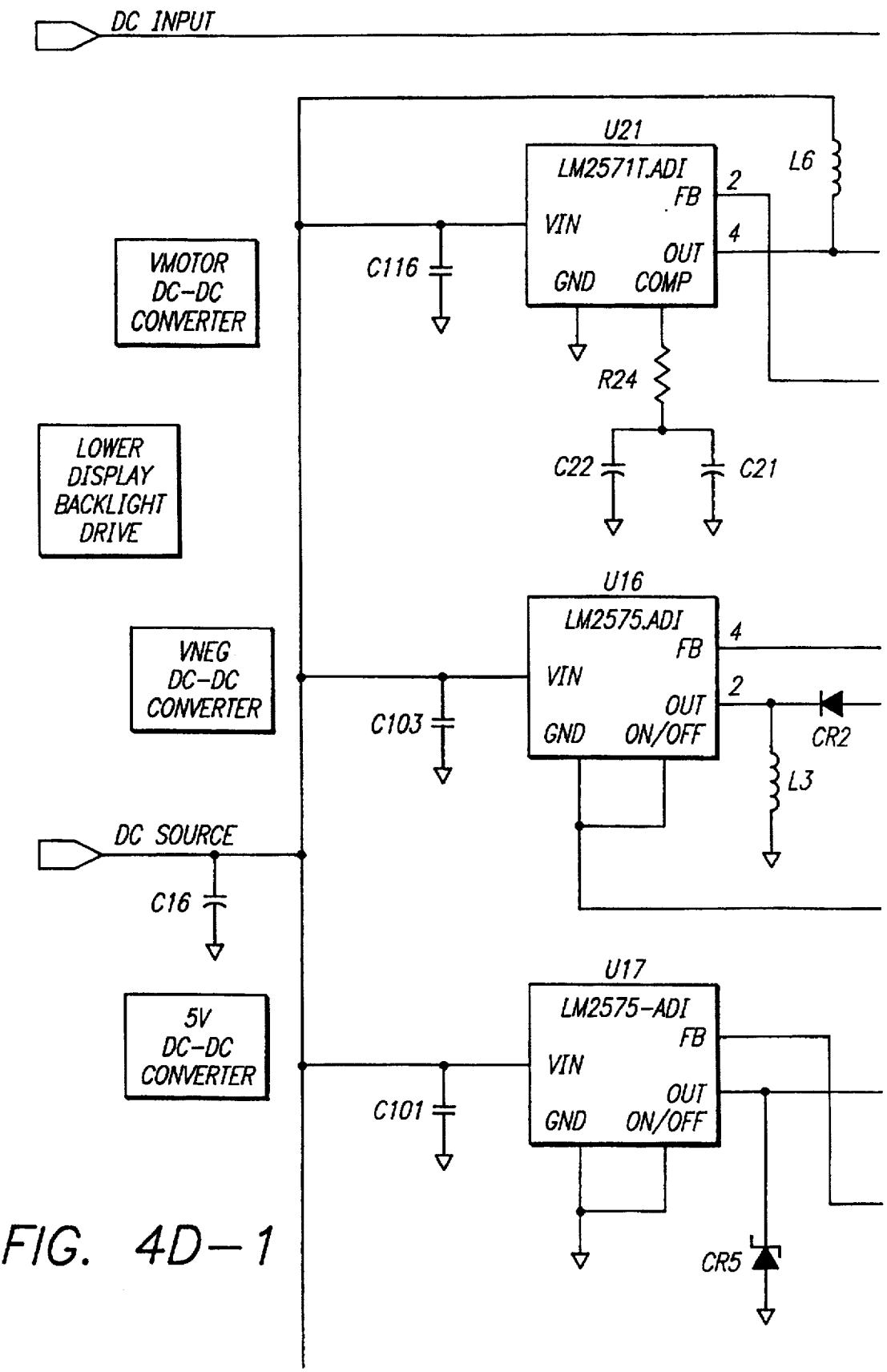
Figure 4D:
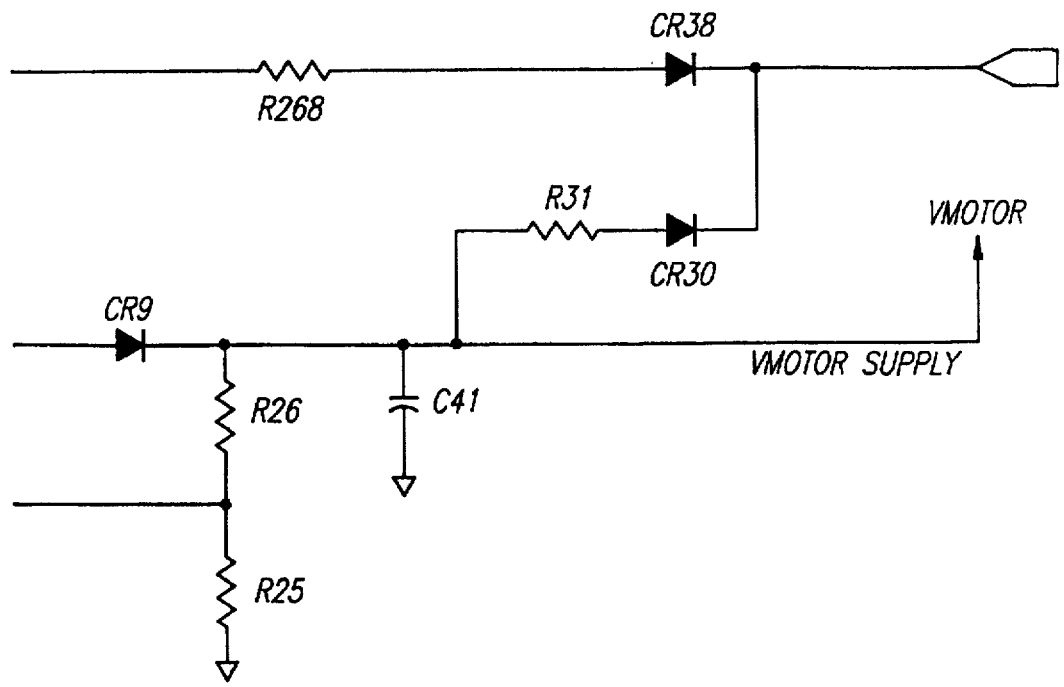
Figure 2:
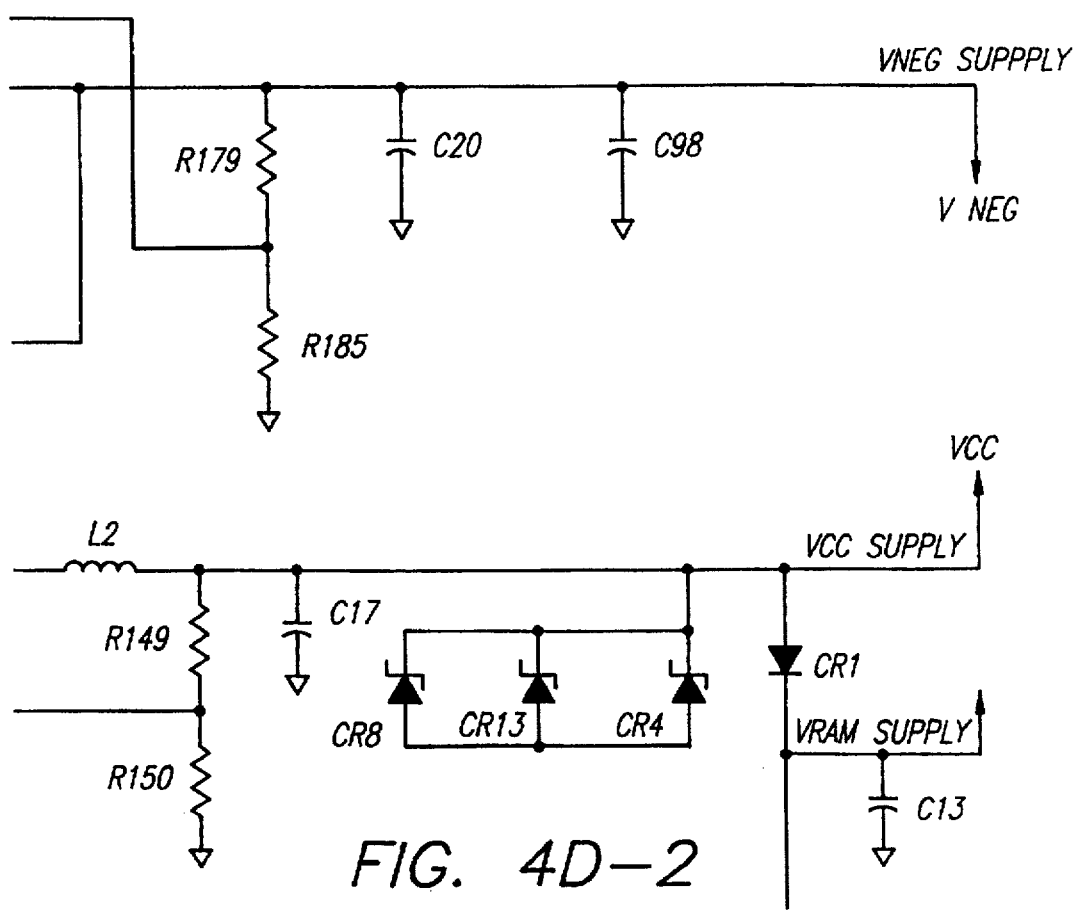
Figures 3, 4D:
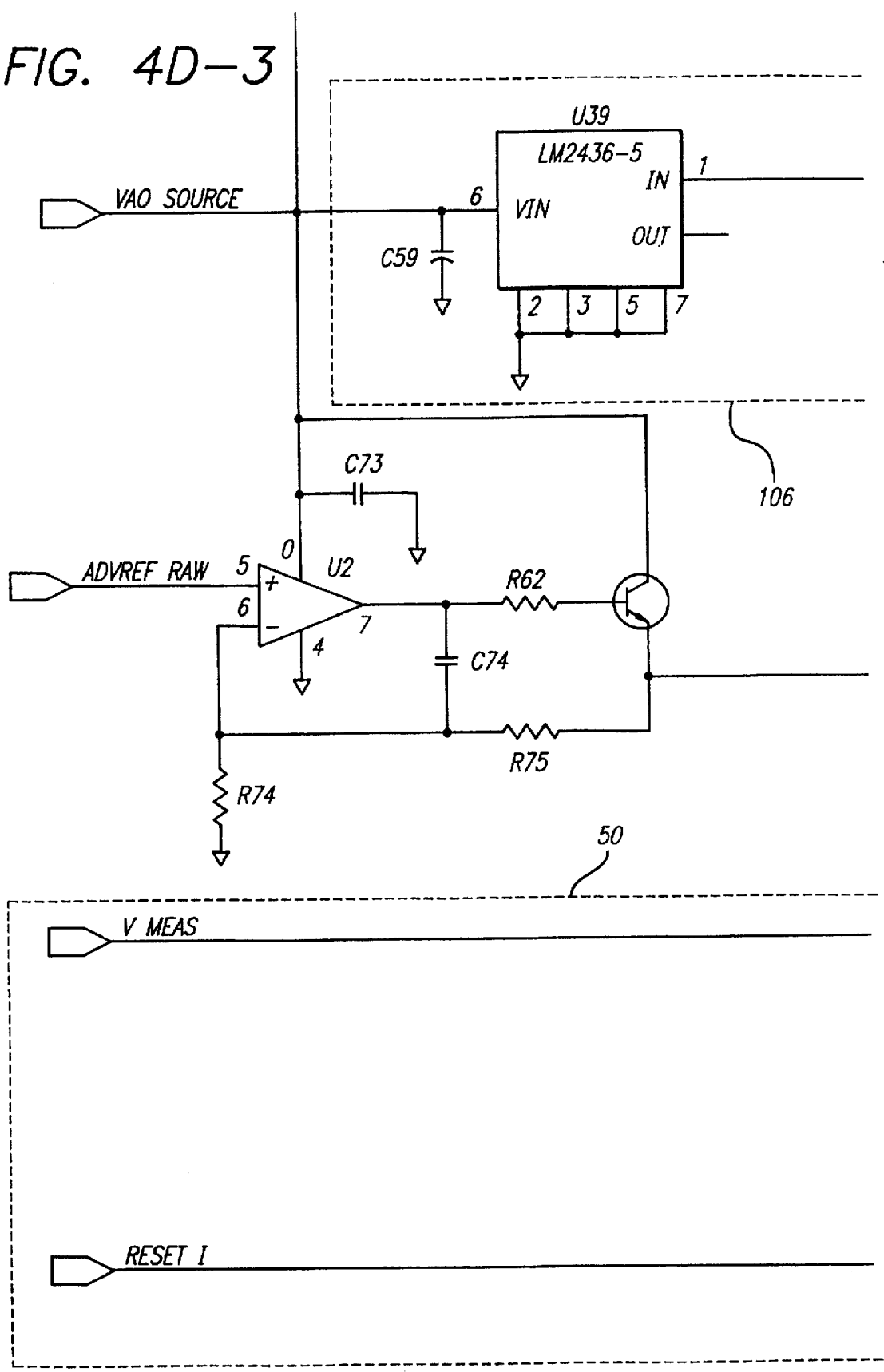
Figure 4D:
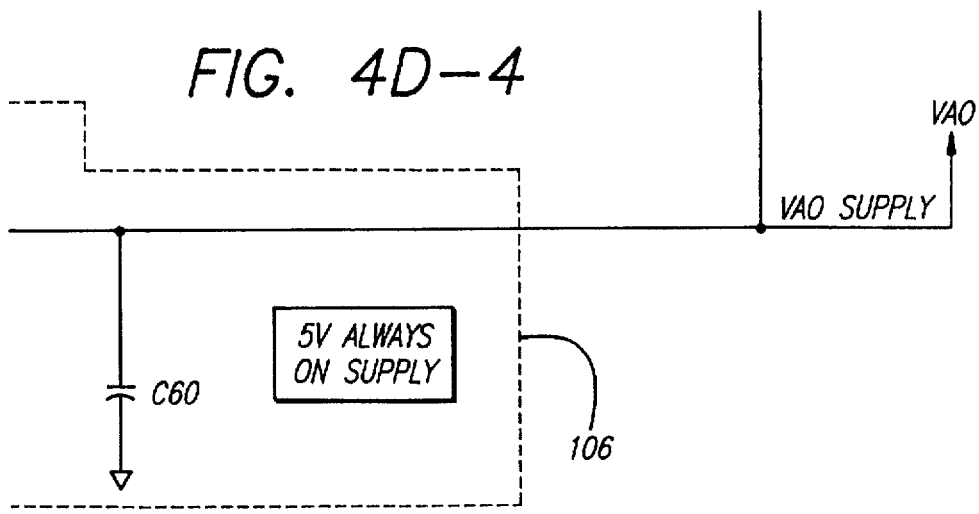
Figure 4:
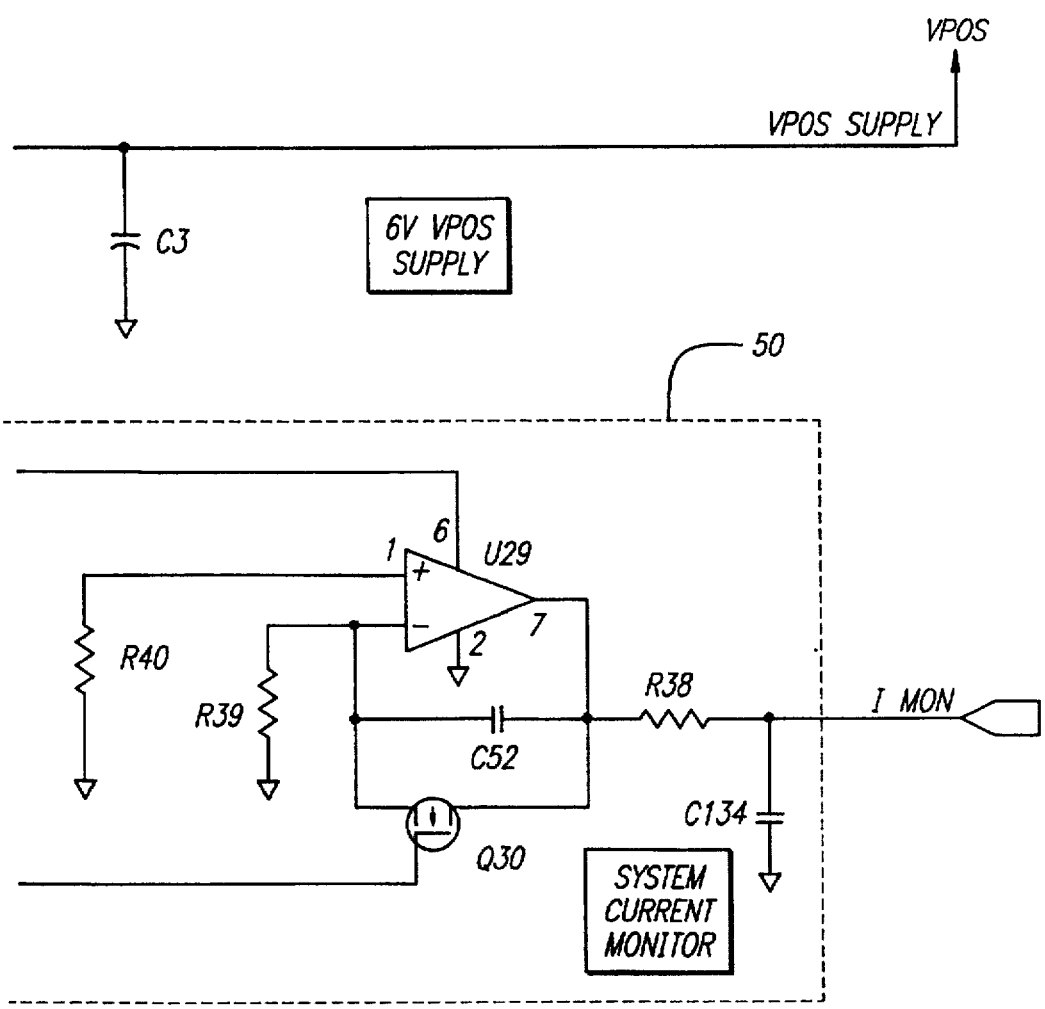
Figure 5:
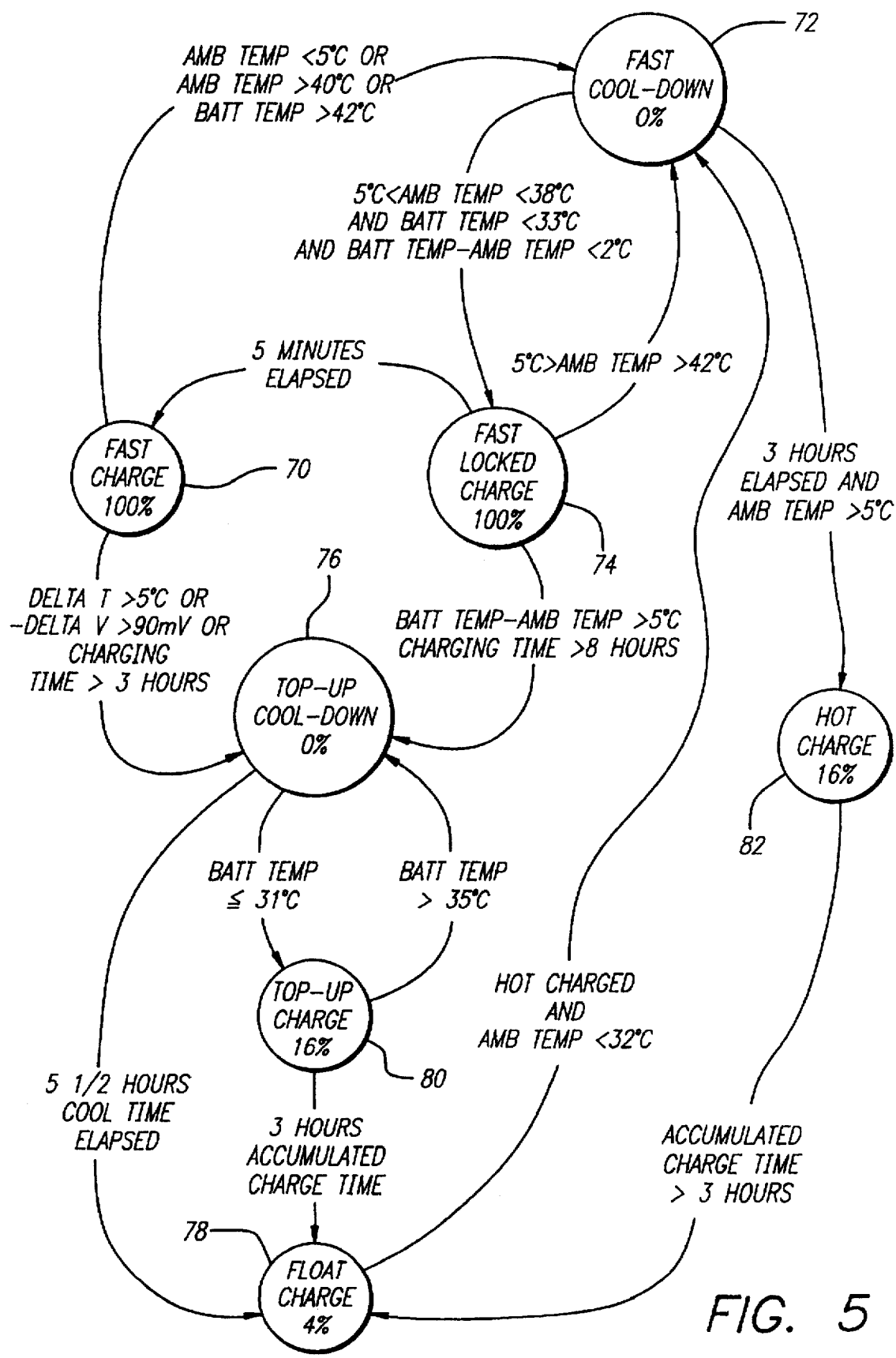

FIG. 5 is a chart illustrating an embodiment of a charge cycle in accordance with principles of the invention. The processor 42 first determines whether an external power source (such as an AC source) is connected to the system. If one is connected and the battery qualifies for recharging, as discussed above, the processor then begins the fast charge cycle at 100% of the fast charge current 70. If the ambient temperature is less than 5° C. or greater than 40° C. or the battery temperature is greater than 42° C., fast charge is stopped and the mode designated as fast cool-down 72 is entered. If the ambient temperature is greater than 5° C. but less than 38° C. and the battery temperature is less than 33° C. and the battery temperature minus the ambient temperature is less than 2° C., the charge cycle proceeds to the Fast Locked Charge at 100% of the fast charge current 74. In the Fast Locked Charge cycle 74, the charge current is applied for 5 minutes and then proceeds to the fast charge cycle 70. However, if the ambient temperature is less than 5° C. or greater than 42° C., the fast cool-down cycle is entered 72. If the battery temperature minus the ambient temperature is greater than 5° C. or the charging time is greater than 8 hours, the fast locked charge 74 proceeds to the top-up cool-down cycle 76. After 5½ hours of cool time elapsed, the float charge cycle 78 is entered. However, if the battery temperature is less than 31° C., the top-up charge cycle 80 is entered where the charge applied to the battery is 16% of the fast charge. During the top-up charge cycle 80, the battery temperature is monitored and if it exceeds 35° C., the top-up cool-down charge cycle 57 is entered. After 3 hours of accumulated charge time in the top-up charge cycle 80, the float charge cycle 78 is entered where the charge applied to the battery is 4% of the fast charge amount.

Returning to the fast charge cycle 70, if the change in temperature of the battery is greater than 5° C. or the negative change in the battery voltage is greater than 90 mV or the charging time is greater than 3 hours, the top-up cool-down cycle 76 is entered.

Returning to the fast cool-down cycle 72, if 3 hours have elapsed and the ambient temperature is greater than 5° C., the hot charge cycle 82 is entered where the charge applied to the battery is 16% of the fast charge amount. After the accumulated time at hot charge exceeds 3 hours, the float charge cycle 78 is entered. However, if the battery is hot charged and the ambient temperature is less than 32° C., the fast cool-down cycle 72 is entered.

While particular embodiments of the invention have been illustrated and described, various modifications can be made without departing from the spirit and scope of the invention. Accordingly, it is not intended that the invention be limited, except as by the appended claims.

We claim:

1. A power management system for managing the power to operate a biomedical device from a rechargeable battery and from an external power source, the biomedical device having a power requirement for operation, the system comprising:

connection means for powering the biomedical device from an external power source when said source is connected to the power management system and for powering the biomedical device from the battery when an external power source is not connected to the power management system;

a charger connected to the battery to provide charge to the battery in response to charge control signals;

a processor that:

provides a charge control signal to the charger to cause the charger to provide charge to the battery when an external power source is connected to the power management system;

automatically determines a value for the amount of charge in the battery;

automatically adjusts the determined value for the amount of charge in the battery based on the number of discharge/charge cycles undergone by the battery;

automatically determines the run time of the battery based on the adjusted determined value of the amount of charge in the battery and the power requirement of the biomedical device;

provides a display signal representative of said run time; and a display that displays the determined run time in response to the display signal.

2. The power management system of claim 1 wherein the processor:

automatically decreases the value for the amount of charge in the battery based on the operation of the biomedical device from the battery; and automatically updates the run time to reflect the decrease in the value for the charge in the battery.

3. The power management system of claim 1 further comprising:

a full charge indicator separate from the run time display that indicates that the battery is fully charged;

wherein the processor illuminates the full charge indicator after the battery charging is complete.

4. The power management system of claim 1 wherein the processor automatically and periodically controls the charger to perform a deep discharge of the battery and to then fully recharge the battery.

5. The power management system of claim 4 wherein the biomedical device is operated from battery power when the processor controls the charger to perform a deep discharge of the battery when the biomedical device is operating.

6. The power management system of claim 1 wherein the processor automatically calculates a decrease in the value for the amount of charge in the battery based on a predetermined rate of self-discharge of the battery.

7. The power management system of claim 1 wherein the processor automatically determines a decrease in the value for the amount of charge in the battery based on a failure to complete a complete charging cycle.

8. The power management system of claim 7 wherein the processor automatically determines an increase in the value for the amount of charge in the battery based on the completion of a complete charging cycle.

9. The power management system of claim 1 wherein the processor automatically adjusts the calculated capacity of the battery to store charge based on the age of the battery.

10. The power management system of claim 1 further comprising an ambient temperature sensor providing an ambient temperature signal to the processor and wherein the processor comprises a value for the charge capacity of the battery; wherein the processor automatically calculates a decrease in the value for said capacity based on the ambient temperature signal at the time of charging the battery.

11. The power management system of claim 1 wherein the processor controls the charger to charge the battery:

in a fast charge cycle in which charge is applied to the battery at a rate that will cause battery damage unless the cycle is limited in time;

in a top-up charge cycle following the fast charge cycle; and in a float charge cycle in which charge lost due to self discharge of the battery is replaced.

12. The power management system of claim 11 further comprising:

an ambient temperature sensor providing an ambient temperature signal to the processor;

wherein the processor controls the charger to charge the battery in a hot charge cycle when the ambient temperature signal indicates that the ambient temperature exceeds a first predetermined threshold, wherein the hot charge cycle comprises applying charge to the battery at a reduced level and for an increased period of time in comparison to the fast charge cycle.

13. A power management system for managing the power to operate a biomedical device from a rechargeable battery and from an external power source, the biomedical device having power requirements that vary depending on the mode of operation selected, the system comprising:

connection means for powering the biomedical device from an external power source when said source is connected to the power management system and for powering the biomedical device from the battery when an external power source is not connected to the power management system;

a charger connected to the battery to provide charge to the battery and to deep discharge the battery in response to charge control signals;

a processor having a memory having a value for the charge capacity of the battery stored in the memory that:

provides a charge control signal to the charger to cause the charger to provide charge to the battery when an external power source is connected to the power management system;

automatically adjusts the value for the charge capacity of the battery stored in the memory based on the number of discharge/charge cycles undergone by the battery;

automatically monitors battery usage to power the biomedical device;

automatically calculates a value for the amount of charge in the battery based on the value for the charge capacity of the battery stored in the memory and automatically updates said value for the amount of charge in the battery based on battery usage;

automatically calculates the run time of the battery based on the calculated value for the amount of charge in the battery and the present power requirement of the biomedical device in the selected mode of operation and automatically updates that run time as the value for the amount of charge and the power requirement of the biomedical device change;

provides a display signal representative of said run time; and a display that displays the determined run time in response to the display signal.

14. The power management system of claim 13 wherein the processor automatically and periodically controls the charger to perform a deep discharge of the battery and to then fully recharge the battery.

15. The power management system of claim 13 wherein the biomedical device is operated from battery power when the processor controls the charger to perform a deep discharge of the battery when the biomedical device is operating.

16. The power management system of claim 15 wherein the biomedical device is operated from battery power when the processor controls the charger to perform a deep discharge of the battery when the biomedical device is operating.

17. The power management system of claim 3 wherein the processor automatically determines a decrease in the value for the amount of charge in the battery based on a failure to complete a complete charging cycle.

18. The power management system of claim 17 wherein the processor automatically determines an increase in the value for the amount of charge in the battery based on the completion of a complete charging cycle.

19. The power management system of claim 3 wherein the processor controls the charger to charge the battery:

in a fast charge cycle in which charge is applied to the battery at a rate that will cause battery damage unless the cycle is limited in time;

in a top-up charge cycle following the fast charge cycle; and in a float charge cycle in which charge lost due to self discharge of the battery is replaced.

20. A method of managing the power for a biomedical device that is connectable to an external power source and which has an internal rechargeable battery, the biomedical device having a power requirement for operation, the method comprising the steps of:

powering the biomedical device from the external power source when the external power source is connected;

powering the biomedical device from the internal battery when the external power source is not connected;

recharging the battery to full charge when the external power source is connected;

automatically determining the charge capacity of the battery based on the number of discharge/charge cycles undergone by the battery;

automatically determining a value for the amount of charge in the battery based on the determined charge capacity of the battery;

automatically determining the run time of the battery based on the determined value of the amount of charge in the battery and the power requirement of the biomedical device; and displaying the amount of run time for the battery.

21. The method of claim 20 further comprising the steps of:

automatically decreasing the value for the amount of charge in the battery based on the operation of the biomedical device from the battery; and automatically updating the run time to reflect the decrease in the value for the charge in the battery.

22. The method of claim 20 further comprising the step of indicating separately from the run time that the battery is fully charged after the battery charging is complete.

23. The method of claim 20 further comprising the step of automatically and periodically deep discharging the battery and then recharging the battery to fully charged status.

24. The method of claim 23 further comprising the step of operating the biomedical device from the battery to cause a deep discharge of the battery when the biomedical device is being operated at the time that the deep discharge cycle of the battery is initiated.

25. The method of claim 20 further comprising the step of automatically calculating a decrease in the value for the amount of charge in the battery based on a predetermined rate of self-discharge of the battery.

26. The method of claim 20 further comprising the steps of:

assigning a value for the battery's charge capacity;

automatically determining a decrease in the value for said capacity based on the ambient temperature at the time of charging the battery.

27. The method of claim 20 further comprising the step of automatically decreasing the value for the amount of charge stored in the battery based on a failure to complete a complete charging cycle.

28. The method of claim 27 further comprising the step of automatically increasing the value for the amount of charge stored in the battery based on the completion of a complete charging cycle.

29. The method of claim 20 further comprising the steps of:

charging the battery in a fast charge cycle in which charge is applied to the battery at a rate that will cause battery damage unless the cycle is limited in time;

charging the battery in a top-up charge cycle following the fast charge cycle; and charging the battery in a float charge cycle in which charge lost due to self discharge of the battery is replaced.

30. The power management system of claim 12 wherein the processor automatically suspends the hot charge cycle in response to the ambient temperature signal indicating an ambient temperature above a second predetermined threshold.

31. The power management system of claim 1 further comprising a memory in which the processor automatically stores a value for battery charge capacity and retains the stored value where the battery is removed from the biomedical device.

32. The power management system of claim 1 further comprising:

a battery voltage sensor that provides a battery voltage signal;

wherein the processor compares the battery voltage signal to a voltage threshold and indicates a battery open condition if the battery voltage signal exceeds the threshold.

33. The power management system of claim 1 further comprising:

a battery voltage sensor that provides a battery voltage signal;

a memory in which is stored data relating stored charge levels to battery voltages;

wherein the processor compares the battery voltage signal and stored charge to corresponding stored data in the memory and if the battery voltage signal indicates a battery voltage significantly less than the stored battery voltage, the processor indicates a battery short condition.

34. The power management system of claim 1 further comprising a memory in which is stored levels of current draw for various operations of the biomedical device;

wherein the processor determines the amount of charge remaining in the battery by determining the current operation of the biomedical device, retrieving the stored current draw from the memory for that operation, and subtracting from the last known charge level of the battery the retrieved current draw level over the time of operation.

35. The power management system of claim 1 further comprising a charge indicator;

wherein the processor flashes the charge indicator during periods when the battery is being charges.

36. The power management system of claim 13 further comprising a memory in which the processor automatically stores a value for battery charge capacity and retains the stored value where the battery is removed from the biomedical device.

37. The power management system of claim 13 further comprising:

a full charge indicator separate from the run time display that indicates that the battery is fully charged;

wherein the processor illuminates the full charge indicator after the battery charging is complete.

38. The power management system of claim 13 further comprising:

a battery voltage sensor that provides a battery voltage signal;

wherein the processor compares the battery voltage signal to a voltage threshold and indicates a battery open condition if the battery voltage signal exceeds the threshold.

39. The power management system of claim 13 further comprising:

a battery voltage sensor that provides a battery voltage signal;

a memory in which is stored data relating stored charge levels to battery voltages;

wherein the processor compares the battery voltage signal and stored charge to corresponding stored data in the memory and if the battery voltage signal indicates a battery voltage significantly less than the stored battery voltage, the processor indicates a battery short condition.

40. The power management system of claim 13 further comprising a memory in which is stored levels of current draw for various operations of the biomedical device;

wherein the processor determines the amount of charge remaining in the battery by determining the current operation of the biomedical device, retrieving the stored current draw from the memory for that operation, and subtracting from the last known charge level of the battery the retrieved current draw level over the time of operation.

41. The power management system of claim 13 further comprising a charge indicator;

wherein the processor flashes the charge indicator during periods when the battery is being charged.

42. The power management system of claim 19 further comprising:

an ambient temperature sensor providing an ambient temperature signal to the processor;

wherein the processor controls the charger to charge the battery in a hot charge cycle when the ambient temperature signal indicates that the ambient temperature exceeds a first predetermined threshold, wherein the hot charge cycle comprises applying charge to the battery at a reduced level and for an increased period of time in comparison to the fast charge cycle.

43. The power management system of claim 42 wherein the processor automatically suspends the hot charge cycle in response to the ambient temperature signal indicating an ambient temperature above a second predetermined threshold.

44. The method of claim 20 further comprising the step of storing a value for battery charge capacity in a memory and retaining the stored value where the battery is removed from the biomedical device.

45. The method of claim 20 further comprising the steps of storing levels of current draw for various operations of the biomedical device;

determining the amount of charge remaining in the battery by determining the current operation of the biomedical device, retrieving the stored current draw from the memory for that operation, and subtracting from the last known charge level of the battery the retrieved current draw level over the time of operation.

46. The method of claim 20 further comprising the step of flashing a charge indicator during periods when the battery is being charged.

47. The method of claim 29 further comprising the steps of:

sensing ambient temperature and providing an ambient temperature signal indicative of the sensed ambient temperature;

charging the battery in a hot charge cycle when the ambient temperature signal indicates that the ambient temperature exceeds a first predetermined threshold, wherein the hot charge cycle comprises applying charge to the battery at a reduced level and for an increased period of time in comparison to the fast charge cycle.

48. The method of claim 47 wherein the step of charging in a hot charge cycle further comprises the step of automatically suspending the hot charge cycle in response to the ambient temperature signal indicating an ambient temperature above a second predetermined threshold.

49. The method of claim 20 further comprising the steps of:

sensing the battery voltage and providing a battery voltage signal;

comparing the battery voltage signal to a voltage threshold and indicating a battery open condition if the battery voltage signal exceeds the threshold.

50. The method of claim 20 further comprising the steps of:

sensing the battery voltage and providing a battery voltage signal;

storing data relating stored charge levels to battery voltages;

comparing the battery voltage signal and stored charge to corresponding stored data in the memory and if the battery voltage signal indicates a battery voltage significantly less than the stored battery voltage, indicating a battery short condition.

51. A power management system for managing the power to operate a biomedical device form a rechargeable battery and from an external power source, the biomedical device having a power requirement for operation, the system comprising:

a charger connected to the battery to provide charge to the battery in response to charge control signals;

an ambient temperature sensor providing an ambient temperature signal;

a processor that automatically controls the charger to charge the battery:

in a fast charge cycle in which charge is applied to the battery at a rate that will cause battery damage unless the cycle is limited in time;

in a top-up charge cycle following the fast charge cycle;

in a float charge cycle in which charge lost due to self discharge of the battery is replaced; and in a hot charge cycle when the ambient temperature signal indicates that the ambient temperature exceeds a first predetermined threshold, wherein the hot charge cycle comprises applying charge to the battery at a reduced level and for an increased period of time in comparison to the fast charge cycle.

52. The power management system of claim 51 wherein the processor automatically suspends the hot charge cycle in response to the ambient temperature signal indicating an ambient temperature above a second predetermined threshold.

* * * * *